(12) United States Patent
Sartor et al.

(10) Patent No.: US 7,766,693 B2
(45) Date of Patent: Aug. 3, 2010

(54) CONNECTOR SYSTEMS FOR ELECTROSURGICAL GENERATOR

(75) Inventors: Joe Don Sartor, Longmont, CO (US); Mark Joseph Huseman, Broomfield, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

(21) Appl. No.: 12/139,914

(22) Filed: Jun. 16, 2008

(65) Prior Publication Data

US 2008/0248685 A1    Oct. 9, 2008

Related U.S. Application Data

(63) Continuation of application No. 11/508,615, filed on Aug. 23, 2006, now Pat. No. 7,416,437, which is a continuation of application No. 10/718,114, filed on Nov. 20, 2003, now Pat. No. 7,131,860.

(51) Int. Cl.
*H01R 3/00* (2006.01)
(52) U.S. Cl. .................................................. 439/489
(58) Field of Classification Search .............. 439/489, 439/909, 912, 218, 219, 692, 650; 606/42, 606/41, 45, 50
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,042,894 A | 7/1962 | Fox |
| 3,058,470 A | 10/1962 | Seeliger et al. |
| 3,083,345 A | 3/1963 | Scheller |
| 3,089,496 A | 5/1963 | Degelman |
| 3,144,292 A | 8/1964 | Forney, Jr. |
| 3,154,365 A | 10/1964 | Crimmins |

(Continued)

FOREIGN PATENT DOCUMENTS

DE    179607    3/1905

(Continued)

OTHER PUBLICATIONS

Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

(Continued)

*Primary Examiner*—Alexander Gilman

(57) ABSTRACT

A connector system for coupling electrosurgical instruments to electrosurgical generators is provided. The connector system includes a plug portion connectable to an electrosurgical instrument, the plug portion of the electrosurgical instrument having a shape specific to a particular manufacturer; and a plug receptacle portion supported on the electrosurgical generator; the plug receptacle portion being shaped to receive the plug portion of the electrosurgical instrument of the particular manufacturer and the plug portion of the electrosurgical instrument of any other manufacturer.

31 Claims, 10 Drawing Sheets

U.S. PATENT DOCUMENTS

| | | | |
|---|---|---|---|
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,901,216 A | 8/1975 | Feiger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,955,869 A | 5/1976 | Licht |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,029,381 A | 6/1977 | Tarrall et al. |
| 4,030,796 A | 6/1977 | Patzer |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,097,104 A | 6/1978 | Furety et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,126 A | 11/1978 | Bare et al. |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,269,462 A | 5/1981 | Bethurum |
| 4,281,373 A | 7/1981 | Mabille |
| 4,284,312 A | 8/1981 | Patchett et al. |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,420,209 A | 12/1983 | Reis et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,518,212 A | 5/1985 | Rumble |
| 4,520,818 A | 6/1985 | Mickiewicz |
| 4,543,448 A | 9/1985 | Deurloo |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |

| | | | | | | |
|---|---|---|---|---|---|---|
| 4,646,222 A | 2/1987 | Okado et al. | | 5,196,008 A | 3/1993 | Kuenecke |
| 4,651,264 A | 3/1987 | Hu | | 5,196,009 A | 3/1993 | Kirwan, Jr. |
| 4,651,280 A | 3/1987 | Chang et al. | | 5,201,900 A | 4/1993 | Nardella |
| 4,657,015 A | 4/1987 | Irnich | | 5,207,691 A | 5/1993 | Nardella |
| 4,658,815 A | 4/1987 | Farin et al. | | 5,211,581 A | 5/1993 | Schwartz et al. |
| 4,658,819 A | 4/1987 | Harris et al. | | 5,230,623 A | 7/1993 | Guthrie et al. |
| 4,658,820 A | 4/1987 | Klicek | | 5,233,515 A | 8/1993 | Cosman |
| 4,662,383 A | 5/1987 | Sogawa et al. | | 5,234,427 A | 8/1993 | Ohtomo et al. |
| 4,691,703 A | 9/1987 | Auth et al. | | 5,244,462 A | 9/1993 | Delahuerga et al. |
| 4,712,559 A | 12/1987 | Turner | | 5,249,121 A | 9/1993 | Baum et al. |
| 4,727,874 A | 3/1988 | Bowers et al. | | 5,249,585 A | 10/1993 | Turner et al. |
| 4,735,204 A | 4/1988 | Sussman et al. | | 5,254,117 A | 10/1993 | Rigby et al. |
| 4,739,759 A | 4/1988 | Rexroth et al. | | RE34,432 E | 11/1993 | Bertrand |
| 4,741,334 A | 5/1988 | Irnich | | 5,267,994 A | 12/1993 | Gentelia et al. |
| 4,746,298 A | 5/1988 | Hollander | | 5,267,997 A | 12/1993 | Farin |
| 4,754,757 A | 7/1988 | Feucht | | 5,281,213 A | 1/1994 | Milder et al. |
| 4,764,129 A | 8/1988 | Jones et al. | | 5,282,840 A | 2/1994 | Hudrlik |
| 4,767,999 A | 8/1988 | VerPlanck | | 5,290,283 A | 3/1994 | Suda |
| 4,768,969 A | 9/1988 | Bauer et al. | | 5,295,857 A | 3/1994 | Toly |
| 4,788,634 A | 11/1988 | Schlecht et al. | | 5,300,068 A | 4/1994 | Rosar et al. |
| 4,805,621 A | 2/1989 | Heinze et al. | | 5,300,070 A | 4/1994 | Gentelia |
| 4,818,954 A | 4/1989 | Flachenecker et al. | | 5,304,917 A | 4/1994 | Somerville |
| 4,827,911 A | 5/1989 | Broadwin et al. | | 5,318,563 A | 6/1994 | Malis et al. |
| 4,827,927 A | 5/1989 | Newton | | 5,323,778 A | 6/1994 | Kandarpa et al. |
| 4,832,024 A | 5/1989 | Boussignac et al. | | 5,324,283 A | 6/1994 | Heckele |
| 4,848,335 A | 7/1989 | Manes | | 5,330,518 A | 7/1994 | Neilson et al. |
| 4,848,355 A | 7/1989 | Nakamura et al. | | 5,334,183 A | 8/1994 | Wuchinich |
| 4,860,745 A | 8/1989 | Farin et al. | | 5,334,193 A | 8/1994 | Nardella |
| 4,862,889 A | 9/1989 | Feucht | | 5,341,807 A | 8/1994 | Nardella |
| 4,880,719 A | 11/1989 | Murofushi et al. | | 5,342,356 A | 8/1994 | Ellman |
| 4,887,199 A | 12/1989 | Whittle | | 5,342,357 A | 8/1994 | Nardella |
| 4,890,610 A | 1/1990 | Kirwan et al. | | 5,342,409 A | 8/1994 | Mullett |
| 4,903,696 A | 2/1990 | Stasz et al. | | 5,346,406 A * | 9/1994 | Hoffman et al. ............ 439/474 |
| 4,907,589 A | 3/1990 | Cosman | | 5,346,491 A | 9/1994 | Oertli |
| 4,922,210 A | 5/1990 | Flachenecker et al. | | 5,348,554 A | 9/1994 | Imran et al. |
| 4,931,047 A | 6/1990 | Broadwin et al. | | 5,370,645 A | 12/1994 | Klicek et al. |
| 4,931,717 A | 6/1990 | Gray et al. | | 5,370,672 A | 12/1994 | Fowler et al. |
| 4,938,761 A | 7/1990 | Ensslin | | 5,370,675 A | 12/1994 | Edwards et al. |
| 4,942,313 A | 7/1990 | Kinzel | | 5,372,596 A | 12/1994 | Klicek et al. |
| 4,959,606 A | 9/1990 | Forge | | 5,376,022 A | 12/1994 | Carr et al. |
| 4,961,047 A | 10/1990 | Carder | | 5,383,874 A | 1/1995 | Jackson |
| 4,961,435 A | 10/1990 | Kitagawa et al. | | 5,383,876 A | 1/1995 | Nardella |
| 4,966,597 A | 10/1990 | Cosman | | 5,383,917 A | 1/1995 | Desai et al. |
| RE33,420 E | 11/1990 | Sussman | | 5,385,148 A | 1/1995 | Lesh et al. |
| 4,969,885 A | 11/1990 | Farin | | 5,396,062 A | 3/1995 | Eisentraut et al. |
| 4,992,719 A | 2/1991 | Harvey | | 5,400,267 A | 3/1995 | Denen et al. |
| 4,993,430 A | 2/1991 | Shimoyama et al. | | 5,403,311 A | 4/1995 | Abele et al. |
| 4,995,877 A | 2/1991 | Ams et al. | | 5,403,312 A | 4/1995 | Yates et al. |
| 5,015,227 A | 5/1991 | Broadwin et al. | | 5,409,000 A | 4/1995 | Imran |
| 5,019,176 A | 5/1991 | Brandhorst, Jr. | | 5,409,006 A | 4/1995 | Buchholtz et al. |
| 5,024,668 A | 6/1991 | Peters et al. | | 5,409,485 A | 4/1995 | Suda |
| 5,029,588 A | 7/1991 | Yock et al. | | 5,413,573 A | 5/1995 | Koivukangas |
| 5,044,977 A * | 9/1991 | Vindigni .................... 439/374 | | 5,414,238 A | 5/1995 | Steigerwald et al. |
| 5,067,953 A | 11/1991 | Feucht | | 5,417,719 A | 5/1995 | Hull et al. |
| 5,075,839 A | 12/1991 | Fisher et al. | | 5,422,567 A | 6/1995 | Matsunaga |
| 5,087,257 A | 2/1992 | Farin et al. | | 5,422,926 A | 6/1995 | Smith et al. |
| 5,088,997 A | 2/1992 | Delahuerga et al. | | 5,423,808 A | 6/1995 | Edwards et al. |
| 5,099,840 A | 3/1992 | Goble et al. | | 5,423,809 A | 6/1995 | Klicek |
| 5,103,804 A | 4/1992 | Abele et al. | | 5,423,810 A | 6/1995 | Goble et al. |
| 5,108,389 A | 4/1992 | Cosmescu | | 5,423,811 A | 6/1995 | Imran et al. |
| 5,108,391 A | 4/1992 | Flachenecker | | 5,425,704 A | 6/1995 | Sakurai et al. |
| 5,119,284 A | 6/1992 | Fisher et al. | | 5,429,596 A | 7/1995 | Arias et al. |
| 5,122,137 A | 6/1992 | Lennox | | 5,430,434 A | 7/1995 | Lederer et al. |
| 5,133,711 A | 7/1992 | Hagen | | 5,432,459 A | 7/1995 | Thompson |
| 5,151,102 A | 9/1992 | Kamiyama et al. | | 5,433,739 A | 7/1995 | Sluijter et al. |
| 5,152,762 A | 10/1992 | McElhenney | | 5,434,398 A | 7/1995 | Goldberg |
| 5,157,603 A | 10/1992 | Scheller et al. | | 5,436,566 A | 7/1995 | Thompson |
| 5,160,334 A | 11/1992 | Billings et al. | | 5,438,302 A | 8/1995 | Goble |
| 5,161,893 A | 11/1992 | Shigezawa et al. | | 5,443,463 A | 8/1995 | Stern et al. |
| 5,162,217 A | 11/1992 | Hartman | | 5,445,635 A | 8/1995 | Denen |
| 5,167,658 A | 12/1992 | Ensslin | | 5,451,224 A | 9/1995 | Goble et al. |
| 5,167,659 A | 12/1992 | Ohtomo et al. | | 5,452,725 A | 9/1995 | Martenson |
| 5,190,517 A | 3/1993 | Zieve et al. | | 5,454,809 A | 10/1995 | Janssen |

| | | | | | |
|---|---|---|---|---|---|
| 5,458,597 A | 10/1995 | Edwards et al. | 5,702,429 A | 12/1997 | King |
| 5,462,521 A | 10/1995 | Brucker et al. | 5,707,369 A | 1/1998 | Vaitekunas et al. |
| 5,472,441 A | 12/1995 | Edwards et al. | 5,712,772 A | 1/1998 | Telefus et al. |
| 5,472,443 A | 12/1995 | Cordis et al. | 5,713,896 A | 2/1998 | Nardella |
| 5,474,464 A * | 12/1995 | Drewnicki ................. 439/172 | 5,718,246 A | 2/1998 | Vona |
| 5,478,303 A | 12/1995 | Folry-Nolan et al. | 5,720,742 A | 2/1998 | Zacharias |
| 5,480,399 A | 1/1996 | Hebborn | 5,720,744 A | 2/1998 | Eggleston et al. |
| 5,483,952 A | 1/1996 | Aranyi | D393,067 S | 3/1998 | Geary et al. |
| 5,496,312 A | 1/1996 | Horner et al. | 5,722,975 A | 3/1998 | Edwards et al. |
| 5,490,850 A | 2/1996 | Ellman et al. | 5,729,448 A | 3/1998 | Haynie et al. |
| 5,496,313 A | 3/1996 | Gentelia et al. | 5,733,281 A | 3/1998 | Nardella |
| 5,496,314 A | 3/1996 | Eggers | 5,735,846 A | 4/1998 | Panescu et al. |
| 5,500,012 A | 3/1996 | Brucker et al. | 5,738,683 A | 4/1998 | Osypka |
| 5,500,616 A | 3/1996 | Ochi | 5,743,900 A | 4/1998 | Hara |
| 5,511,993 A | 4/1996 | Yamada et al. | 5,743,903 A | 4/1998 | Stern et al. |
| 5,514,129 A | 5/1996 | Smith | 5,749,869 A | 5/1998 | Lindenmeier et al. |
| 5,520,684 A | 5/1996 | Imran | 5,749,871 A | 5/1998 | Hood et al. |
| 5,531,774 A | 7/1996 | Schulman et al. | 5,755,715 A | 5/1998 | Stern |
| 5,534,018 A | 7/1996 | Wahlstrand et al. | 5,766,153 A | 6/1998 | Eggers et al. |
| 5,536,267 A | 7/1996 | Edwards et al. | 5,766,165 A | 6/1998 | Gentelia et al. |
| 5,540,677 A | 7/1996 | Sinofsky | 5,769,847 A | 6/1998 | Panescu |
| 5,540,681 A | 7/1996 | Strul et al. | 5,772,659 A | 6/1998 | Becker et al. |
| 5,540,682 A | 7/1996 | Gardner et al. | 5,788,688 A | 8/1998 | Bauer et al. |
| 5,540,683 A | 7/1996 | Ichikawa | 5,792,138 A | 8/1998 | Shipp |
| 5,540,684 A | 7/1996 | Hassler, Jr. | 5,797,902 A | 8/1998 | Netherly |
| 5,540,724 A | 7/1996 | Cox | 5,807,253 A | 9/1998 | Dumoulin et al. |
| 5,541,376 A | 7/1996 | Ladtkow et al. | 5,810,804 A | 9/1998 | Gough et al. |
| 5,545,161 A | 8/1996 | Imran | 5,814,092 A | 9/1998 | King |
| 5,556,396 A | 9/1996 | Cohen et al. | 5,817,091 A | 10/1998 | Nardella et al. |
| 5,558,671 A | 9/1996 | Yates | 5,817,092 A | 10/1998 | Behl |
| 5,562,720 A | 10/1996 | Stern et al. | 5,817,093 A | 10/1998 | Williamson, IV et al. |
| 5,569,242 A | 10/1996 | Lax et al. | 5,820,568 A | 10/1998 | Willis |
| 5,571,147 A | 11/1996 | Sluijter et al. | 5,827,271 A | 10/1998 | Bussey et al. |
| 5,573,533 A | 11/1996 | Strul | 5,830,212 A | 11/1998 | Cartmell |
| 5,584,830 A | 12/1996 | Ladd et al. | 5,836,909 A | 11/1998 | Cosmescu |
| 5,588,432 A | 12/1996 | Crowley | 5,836,943 A | 11/1998 | Miller, III |
| 5,594,636 A | 1/1997 | Schauder | 5,836,990 A | 11/1998 | Li |
| 5,596,466 A | 1/1997 | Ochi | 5,843,019 A | 12/1998 | Eggers et al. |
| 5,599,344 A | 2/1997 | Paterson | 5,843,075 A | 12/1998 | Taylor |
| 5,599,345 A | 2/1997 | Edwards et al. | 5,846,236 A | 12/1998 | Lindenmeier et al. |
| 5,599,348 A | 2/1997 | Gentelia et al. | 5,849,010 A | 12/1998 | Wurzer et al. |
| 5,605,150 A | 2/1997 | Radons et al. | 5,853,409 A | 12/1998 | Swanson et al. |
| 5,609,560 A | 3/1997 | Ichikawa et al. | 5,860,832 A | 1/1999 | Wayt et al. |
| 5,613,966 A | 3/1997 | Makower et al. | 5,865,788 A | 2/1999 | Edwards et al. |
| 5,613,996 A | 3/1997 | Lindsay | 5,868,737 A | 2/1999 | Taylor et al. |
| 5,620,481 A | 4/1997 | Desai et al. | 5,868,739 A | 2/1999 | Lindenmeier et al. |
| 5,625,370 A | 4/1997 | D'Hont | 5,868,740 A | 2/1999 | LeVeen et al. |
| 5,626,575 A | 5/1997 | Crenner | 5,871,481 A | 2/1999 | Kannenberg et al. |
| 5,628,745 A | 5/1997 | Bek | 5,891,142 A | 4/1999 | Eggers et al. |
| 5,628,771 A | 5/1997 | Mizukawa et al. | 5,897,552 A | 4/1999 | Edwards et al. |
| 5,643,330 A | 7/1997 | Holsheimer et al. | 5,906,614 A | 5/1999 | Stern et al. |
| 5,647,869 A | 7/1997 | Goble et al. | 5,908,444 A | 6/1999 | Azure |
| 5,647,871 A | 7/1997 | Levine et al. | 5,913,882 A | 6/1999 | King |
| 5,651,780 A | 7/1997 | Jackson et al. | 5,921,982 A | 7/1999 | Lesh et al. |
| 5,658,173 A | 8/1997 | Genta | 5,925,070 A | 7/1999 | King et al. |
| 5,658,322 A | 8/1997 | Fleming | 5,931,836 A | 8/1999 | Hatta et al. |
| 5,660,567 A * | 8/1997 | Nierlich et al. ........ 439/620.21 | 5,938,690 A | 8/1999 | Law et al. |
| 5,664,953 A | 9/1997 | Reylek | 5,944,553 A | 8/1999 | Yasui et al. |
| 5,674,217 A | 10/1997 | Wahlstrom et al. | 5,948,007 A | 9/1999 | Starkebaum et al. |
| 5,678,568 A | 10/1997 | Uchikubo et al. | 5,951,545 A | 9/1999 | Schilling |
| 5,681,307 A | 10/1997 | McMahan | 5,951,546 A | 9/1999 | Lorentzen |
| 5,685,840 A | 11/1997 | Schechter et al. | 5,954,686 A | 9/1999 | Garito et al. |
| 5,688,267 A | 11/1997 | Panescu et al. | 5,954,717 A | 9/1999 | Behl et al. |
| 5,690,692 A | 11/1997 | Fleming | 5,954,719 A | 9/1999 | Chen et al. |
| 5,693,042 A | 12/1997 | Bioarski et al. | 5,957,961 A | 9/1999 | Maguire et al. |
| 5,693,078 A | 12/1997 | Desai et al. | 5,959,253 A | 9/1999 | Shinchi |
| 5,694,304 A | 12/1997 | Telefus et al. | 5,961,344 A | 10/1999 | Rosales et al. |
| 5,695,494 A | 12/1997 | Becker | 5,964,746 A | 10/1999 | McCary |
| 5,696,351 A | 12/1997 | Benn et al. | 5,971,784 A | 10/1999 | Fabian et al. |
| 5,696,441 A | 12/1997 | Mak et al. | 5,971,980 A | 10/1999 | Sherman |
| 5,697,925 A | 12/1997 | Taylor | 5,971,981 A | 10/1999 | Hill et al. |
| 5,697,927 A | 12/1997 | Imran et al. | 5,976,128 A | 11/1999 | Schilling et al. |
| 5,702,386 A | 12/1997 | Stern et al. | 5,983,141 A | 11/1999 | Sluijter et al. |

| | | | | | | |
|---|---|---|---|---|---|---|
| 6,007,532 | A | 12/1999 | Netherly | 6,261,129 B1 | 7/2001 | Kusagaya |
| 6,010,499 | A | 1/2000 | Cobb | 6,261,285 B1 | 7/2001 | Novak |
| 6,013,074 | A | 1/2000 | Taylor | 6,261,286 B1 | 7/2001 | Goble et al. |
| 6,014,581 | A | 1/2000 | Whayne et al. | 6,267,760 B1 | 7/2001 | Swanson |
| 6,017,338 | A | 1/2000 | Brucker et al. | 6,273,886 B1 | 8/2001 | Edwards |
| 6,022,346 | A | 2/2000 | Panescu et al. | 6,275,786 B1 | 8/2001 | Daners |
| 6,022,347 | A | 2/2000 | Lindenmeier et al. | 6,293,941 B1 | 9/2001 | Strul |
| 6,033,399 | A | 3/2000 | Gines | 6,293,942 B1 | 9/2001 | Goble et al. |
| 6,039,731 | A | 3/2000 | Taylor et al. | 6,293,943 B1 | 9/2001 | Panescu et al. |
| 6,039,732 | A | 3/2000 | Ichikawa et al. | 6,296,636 B1 | 10/2001 | Cheng et al. |
| 6,041,260 | A | 3/2000 | Stern et al. | 6,306,131 B1 | 10/2001 | Hareyama et al. |
| 6,044,283 | A | 3/2000 | Fein et al. | 6,306,134 B1 | 10/2001 | Goble et al. |
| 6,053,910 | A | 4/2000 | Fleenor | 6,309,386 B1 | 10/2001 | Bek |
| 6,053,912 | A | 4/2000 | Panescu et al. | 6,316,778 B1 | 11/2001 | Goodman et al. |
| 6,055,458 | A | 4/2000 | Cochran et al. | 6,322,558 B1 | 11/2001 | Taylor et al. |
| 6,056,745 | A | 5/2000 | Panescu et al. | 6,325,795 B1 | 12/2001 | Lindemann et al. |
| 6,056,746 | A | 5/2000 | Goble et al. | 6,325,799 B1 | 12/2001 | Goble |
| 6,059,781 | A | 5/2000 | Yamanashi et al. | 6,337,998 B1 | 1/2002 | Behl et al. |
| 6,063,075 | A | 5/2000 | Mihori | 6,338,657 B1 * | 1/2002 | Harper et al. ............... 439/692 |
| 6,063,078 | A | 5/2000 | Wittkampf | 6,350,262 B1 | 2/2002 | Ashley |
| 6,066,137 | A | 5/2000 | Greep | 6,358,245 B1 | 3/2002 | Edwards |
| 6,068,627 | A * | 5/2000 | Orszulak et al. ............... 606/34 | 6,364,877 B1 | 4/2002 | Goble et al. |
| 6,074,089 | A | 6/2000 | Hollander et al. | 6,368,106 B1 | 4/2002 | Clark |
| 6,074,386 | A | 6/2000 | Goble et al. | 6,371,963 B1 | 4/2002 | Nishtala et al. |
| 6,074,388 | A | 6/2000 | Tockweiler et al. | 6,383,183 B1 | 5/2002 | Sekino et al. |
| 6,080,149 | A | 6/2000 | Huang et al. | 6,391,024 B1 | 5/2002 | Sun et al. |
| 6,088,614 | A | 7/2000 | Swanson | 6,398,779 B1 | 6/2002 | Buysse et al. |
| 6,093,186 | A | 7/2000 | Goble | 6,398,781 B1 | 6/2002 | Goble et al. |
| 6,102,497 | A | 8/2000 | Ehr et al. | 6,402,741 B1 | 6/2002 | Keppel et al. |
| 6,102,907 | A | 8/2000 | Smethers et al. | 6,402,742 B1 | 6/2002 | Blewett et al. |
| RE36,871 | E | 9/2000 | Epstein | 6,402,743 B1 | 6/2002 | Orszulak et al. |
| 6,113,591 | A | 9/2000 | Whayne et al. | 6,402,747 B1 | 6/2002 | Lindemann et al. |
| 6,113,592 | A | 9/2000 | Taylor | 6,402,748 B1 * | 6/2002 | Schoenman et al. ........... 606/45 |
| 6,113,593 | A | 9/2000 | Tu et al. | 6,409,533 B1 | 6/2002 | Savage, Jr. |
| 6,113,596 | A | 9/2000 | Hooven | 6,409,549 B1 | 6/2002 | Yeh |
| 6,123,701 | A | 9/2000 | Nezhat | 6,409,722 B1 | 6/2002 | Hoey et al. |
| 6,123,702 | A | 9/2000 | Swanson et al. | 6,413,256 B1 | 7/2002 | Truckai et al. |
| 6,132,429 | A | 10/2000 | Baker | 6,416,509 B1 | 7/2002 | Goble et al. |
| 6,142,992 | A | 11/2000 | Cheng et al. | 6,422,896 B2 | 7/2002 | Aoki et al. |
| 6,155,975 | A | 12/2000 | Urich et al. | 6,423,057 B1 | 7/2002 | He et al. |
| 6,162,184 | A | 12/2000 | Swanson et al. | 6,426,886 B1 | 7/2002 | Goder |
| 6,162,217 | A | 12/2000 | Kannenberg et al. | 6,428,537 B1 | 8/2002 | Swanson et al. |
| 6,165,169 | A | 12/2000 | Panescu et al. | 6,436,096 B1 | 8/2002 | Hareyama |
| 6,171,304 | B1 | 1/2001 | Netherly et al. | 6,440,157 B1 | 8/2002 | Shigezawa et al. |
| 6,183,468 | B1 | 2/2001 | Swanson et al. | 6,451,015 B1 | 9/2002 | Rittman, III et al. |
| 6,186,147 | B1 | 2/2001 | Cobb | 6,454,594 B2 | 9/2002 | Sawayanagi |
| 6,188,211 | B1 | 2/2001 | Rincon-Mora et al. | 6,458,000 B2 | 10/2002 | Shappell |
| 6,193,713 | B1 | 2/2001 | Geistert et al. | 6,458,121 B1 | 10/2002 | Rosenstock |
| 6,197,023 | B1 | 3/2001 | Muntermann | 6,458,122 B1 | 10/2002 | Pozzato |
| 6,203,541 | B1 | 3/2001 | Keppel | 6,464,689 B1 | 10/2002 | Qin |
| 6,210,403 | B1 | 4/2001 | Klicek | 6,464,696 B1 | 10/2002 | Oyama |
| 6,216,704 | B1 | 4/2001 | Ingle et al. | 6,468,270 B1 | 10/2002 | Hovda et al. |
| 6,222,356 | B1 | 4/2001 | Taghizadeh-Kaschani | 6,468,273 B1 | 10/2002 | Leveen et al. |
| 6,228,078 | B1 | 5/2001 | Eggers et al. | 6,482,201 B1 | 11/2002 | Olsen et al. |
| 6,228,080 | B1 | 5/2001 | Gines | 6,488,678 B2 | 12/2002 | Sherman |
| 6,228,081 | B1 | 5/2001 | Goble | 6,494,880 B1 | 12/2002 | Swanson et al. |
| 6,231,569 | B1 | 5/2001 | Bek | 6,497,659 B1 | 12/2002 | Rafert |
| 6,232,556 | B1 | 5/2001 | Daugherty et al. | 6,498,466 B1 | 12/2002 | Edwards |
| 6,235,020 | B1 | 5/2001 | Cheng et al. | 6,506,189 B1 | 1/2003 | Rittman, III et al. |
| 6,235,022 | B1 | 5/2001 | Hallock et al. | 6,508,815 B1 | 1/2003 | Strul |
| 6,237,604 | B1 | 5/2001 | Burnside et al. | 6,511,476 B2 | 1/2003 | Hareyama |
| 6,238,387 | B1 | 5/2001 | Miller, III | 6,511,478 B1 | 1/2003 | Burnside |
| 6,238,388 | B1 | 5/2001 | Ellman | 6,517,538 B1 | 2/2003 | Jacob et al. |
| 6,241,723 | B1 | 6/2001 | Heim et al. | 6,520,787 B1 | 2/2003 | Lott |
| 6,241,725 | B1 | 6/2001 | Cosman | 6,522,931 B2 | 2/2003 | Manker et al. |
| 6,243,654 | B1 | 6/2001 | Johnson et al. | 6,524,308 B1 | 2/2003 | Muller et al. |
| 6,245,061 | B1 | 6/2001 | Panescu et al. | 6,537,272 B2 | 3/2003 | Christopherson et al. |
| 6,245,063 | B1 | 6/2001 | Uphoff | 6,544,076 B2 | 4/2003 | Pocrass |
| 6,245,065 | B1 | 6/2001 | Panescu | 6,544,260 B1 | 4/2003 | Markel et al. |
| 6,246,912 | B1 | 6/2001 | Sluijter et al. | 6,546,270 B1 | 4/2003 | Goldin et al. |
| 6,251,106 | B1 | 6/2001 | Becker et al. | 6,547,786 B1 | 4/2003 | Goble |
| 6,254,422 | B1 | 7/2001 | Feye-Hohmann | 6,557,559 B1 | 5/2003 | Eggers et al. |
| 6,258,085 | B1 | 7/2001 | Eggleston | 6,558,203 B2 | 5/2003 | Pocrass |

| | | |
|---|---|---|
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,568,965 B2 | 5/2003 | Pocrass |
| 6,573,248 B2 | 6/2003 | Ramasamy et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,579,644 B2 | 6/2003 | Hasegawa et al. |
| 6,582,427 B1 | 6/2003 | Goble et al. |
| 6,595,805 B2 | 7/2003 | Pocrass |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,654,643 B1 | 11/2003 | Schmid |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,311 B1 | 2/2004 | Kamei et al. |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 * | 6/2004 | Spink, Jr. .................... 439/740 |
| 6,749,451 B2 | 6/2004 | Schmitt |
| 6,749,624 B2 | 6/2004 | Knowlton |
| 6,755,825 B2 | 6/2004 | Shoenman et al. |
| 6,758,700 B2 | 7/2004 | Konno et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,777 B2 | 9/2004 | Sakatani |
| 6,786,905 B2 | 9/2004 | Swanson et al. |
| 6,786,906 B1 | 9/2004 | Cobb |
| 6,786,909 B1 | 9/2004 | Dransfeld et al. |
| 6,790,206 B2 | 9/2004 | Panescu |
| 6,792,390 B1 | 9/2004 | Burnside et al. |
| 6,796,849 B2 | 9/2004 | Villain |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,835,082 B2 | 12/2004 | Gonnering |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,849,073 B2 | 2/2005 | Hoey |
| 6,854,994 B2 | 2/2005 | Stein et al. |
| 6,855,141 B2 | 2/2005 | Lovewell |
| 6,855,142 B2 | 2/2005 | Harano |
| 6,857,903 B2 | 2/2005 | Hyde |
| 6,860,881 B2 | 3/2005 | Sturm |
| 6,875,210 B2 | 4/2005 | Refior |
| 6,890,220 B2 | 5/2005 | Wang |
| 6,890,331 B2 | 5/2005 | Kristensen |
| 6,893,435 B2 | 5/2005 | Goble |
| 6,899,538 B2 | 5/2005 | Matoba |
| 6,864,686 B2 | 8/2005 | Novak |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |

| | | | | | |
|---|---|---|---|---|---|
| 7,151,964 B2 | 12/2006 | Desai et al. | 2002/0068932 A1 | 6/2002 | Edwards |
| 7,153,300 B2 | 12/2006 | Goble | 2002/0107517 A1 | 8/2002 | Witt et al. |
| 7,156,844 B2 | 1/2007 | Reschke et al. | 2002/0111624 A1 | 8/2002 | Witt et al. |
| 7,156,846 B2 | 1/2007 | Dycus et al. | 2002/0151889 A1 | 10/2002 | Swanson et al. |
| 7,160,293 B2 | 1/2007 | Sturm et al. | 2002/0193787 A1 | 12/2002 | Qin |
| 7,163,536 B2 | 1/2007 | Godara | 2003/0004510 A1 | 1/2003 | Wham et al. |
| 7,169,144 B2 | 1/2007 | Hoey et al. | 2003/0060818 A1 | 3/2003 | Kannenberg |
| 7,172,591 B2 | 2/2007 | Harano et al. | 2003/0078572 A1 | 4/2003 | Pearson et al. |
| 7,175,618 B2 | 2/2007 | Dabney et al. | 2003/0139741 A1 | 7/2003 | Goble et al. |
| 7,175,621 B2 | 2/2007 | Heim et al. | 2003/0153908 A1 | 8/2003 | Goble |
| 7,192,427 B2 | 3/2007 | Chapelon et al. | 2003/0163123 A1 | 8/2003 | Goble |
| 7,195,627 B2 | 3/2007 | Amoah et al. | 2003/0163124 A1 | 8/2003 | Goble |
| 7,203,556 B2 | 4/2007 | Daners | 2003/0171745 A1 | 9/2003 | Francischelli |
| 7,211,081 B2 | 5/2007 | Goble | 2003/0181898 A1 | 9/2003 | Bowers |
| 7,214,224 B2 | 5/2007 | Goble | 2003/0199863 A1 | 10/2003 | Swanson |
| 7,217,269 B2 | 5/2007 | El-Galley et al. | 2003/0225401 A1 | 12/2003 | Eggers et al. |
| 7,220,260 B2 | 5/2007 | Fleming et al. | 2004/0002745 A1 | 1/2004 | Fleming |
| 7,223,264 B2 | 5/2007 | Daniel et al. | 2004/0015159 A1 | 1/2004 | Slater et al. |
| 7,226,447 B2 | 6/2007 | Uchida et al. | 2004/0015163 A1 | 1/2004 | Buysse et al. |
| 7,229,469 B1 | 6/2007 | Witzel et al. | 2004/0015216 A1 | 1/2004 | DeSisto |
| 7,232,437 B2 | 6/2007 | Berman et al. | 2004/0019347 A1 | 1/2004 | Sakurai |
| 7,238,181 B2 | 7/2007 | Daners et al. | 2004/0024395 A1 | 2/2004 | Ellman |
| 7,238,183 B2 | 7/2007 | Kreindel | 2004/0030328 A1 | 2/2004 | Eggers |
| 7,244,255 B2 | 7/2007 | Daners et al. | 2004/0030330 A1* | 2/2004 | Brassell et al. ................ 606/41 |
| 7,247,155 B2 | 7/2007 | Hoey et al. | 2004/0044339 A1 | 3/2004 | Beller |
| 7,250,048 B2 | 7/2007 | Francischelli et al. | 2004/0049179 A1 | 3/2004 | Francischelli |
| 7,250,746 B2 | 7/2007 | Oswald et al. | 2004/0054365 A1 | 3/2004 | Goble |
| 7,255,694 B2 | 8/2007 | Keppel | 2004/0059323 A1 | 3/2004 | Sturm et al. |
| 7,258,688 B1 | 8/2007 | Shah et al. | 2004/0068304 A1 | 4/2004 | Paton |
| 7,282,048 B2 | 10/2007 | Goble et al. | 2004/0082946 A1 | 4/2004 | Malis |
| 7,282,049 B2 | 10/2007 | Orszulak et al. | 2004/0095100 A1 | 5/2004 | Thompson |
| 7,285,117 B2 | 10/2007 | Krueger et al. | 2004/0097912 A1 | 5/2004 | Gonnering |
| 7,294,127 B2 | 11/2007 | Leung et al. | 2004/0097914 A1 | 5/2004 | Pantera |
| 7,300,435 B2 | 11/2007 | Wham et al. | 2004/0097915 A1 | 5/2004 | Refior |
| 7,300,437 B2 | 11/2007 | Pozzato | 2004/0116919 A1 | 6/2004 | Heim |
| 7,303,557 B2 | 12/2007 | Wham et al. | 2004/0133189 A1 | 7/2004 | Sakurai |
| 7,305,311 B2 | 12/2007 | Van Zyl | 2004/0138653 A1 | 7/2004 | Dabney et al. |
| 7,317,954 B2 | 1/2008 | McGreevy | 2004/0138654 A1 | 7/2004 | Goble |
| 7,317,955 B2 | 1/2008 | McGreevy | 2004/0143263 A1 | 7/2004 | Schechter et al. |
| 7,324,357 B2 | 1/2008 | Miura et al. | 2004/0147918 A1 | 7/2004 | Keppel |
| 7,333,859 B2 | 2/2008 | Rinaldi et al. | 2004/0167508 A1 | 8/2004 | Wham et al. |
| 7,341,586 B2 | 3/2008 | Daniel et al. | 2004/0172016 A1 | 9/2004 | Bek et al. |
| 7,344,532 B2 | 3/2008 | Goble et al. | 2004/0193148 A1 | 9/2004 | Wham et al. |
| 7,353,068 B2 | 4/2008 | Tanaka et al. | 2004/0230189 A1 | 11/2004 | Keppel |
| 7,354,436 B2 | 4/2008 | Rioux et al. | 2004/0243120 A1 | 12/2004 | Orszulak et al. |
| 7,357,800 B2 | 4/2008 | Swanson | 2004/0260279 A1 | 12/2004 | Goble |
| 7,364,577 B2 | 4/2008 | Wham et al. | 2005/0004564 A1 | 1/2005 | Wham |
| 7,364,578 B2 | 4/2008 | Francischelli et al. | 2005/0004569 A1 | 1/2005 | Witt et al. |
| 7,364,972 B2 | 4/2008 | Ono et al. | 2005/0004634 A1 | 1/2005 | Ricart et al. |
| 7,367,972 B2 | 5/2008 | Francischelli et al. | 2005/0021020 A1 | 1/2005 | Blaha et al. |
| RE40,388 E | 6/2008 | Gines | 2005/0021022 A1 | 1/2005 | Sturm et al. |
| 7,396,336 B2 | 7/2008 | Orszulak et al. | 2005/0101949 A1 | 5/2005 | Harano et al. |
| 7,402,754 B2 | 7/2008 | Kirwan, Jr. et al. | 2005/0101951 A1 | 5/2005 | Wham |
| D574,323 S | 8/2008 | Waaler | 2005/0109111 A1 | 5/2005 | Manlove et al. |
| 7,407,502 B2 | 8/2008 | Strul et al. | 2005/0113818 A1 | 5/2005 | Sartor |
| 7,416,437 B2 | 8/2008 | Sartor et al. | 2005/0113819 A1 | 5/2005 | Wham |
| 7,416,549 B2 | 8/2008 | Young et al. | 2005/0149151 A1 | 7/2005 | Orszulak |
| 7,422,582 B2 | 9/2008 | Malackowski et al. | 2005/0182398 A1 | 8/2005 | Paterson |
| 7,422,586 B2 | 9/2008 | Morris et al. | 2005/0197659 A1 | 9/2005 | Bahney |
| 7,425,835 B2 | 9/2008 | Eisele | 2005/0203504 A1 | 9/2005 | Wham et al. |
| 7,465,302 B2 | 12/2008 | Odell et al. | 2006/0025760 A1 | 2/2006 | Podhajsky |
| 7,470,272 B2 | 12/2008 | Mulier et al. | 2006/0079871 A1 | 4/2006 | Plaven et al. |
| 7,479,140 B2 | 1/2009 | Ellman et al. | 2006/0111711 A1 | 5/2006 | Goble |
| 7,491,199 B2 | 2/2009 | Goble | 2006/0161148 A1 | 7/2006 | Behnke |
| 7,491,201 B2 | 2/2009 | Shields et al. | 2006/0178664 A1 | 8/2006 | Keppel |
| 7,513,896 B2 | 4/2009 | Orszulak | 2006/0224152 A1 | 10/2006 | Behnke et al. |
| 7,525,398 B2 | 4/2009 | Nishimura et al. | 2006/0281360 A1 | 12/2006 | Sartor et al. |
| 2001/0014804 A1 | 8/2001 | Goble et al. | 2006/0291178 A1 | 12/2006 | Shih |
| 2001/0029315 A1 | 10/2001 | Sakurai et al. | 2007/0038209 A1 | 2/2007 | Buysse et al. |
| 2001/0031962 A1 | 10/2001 | Eggleston | 2007/0093800 A1 | 4/2007 | Wham et al. |
| 2002/0035363 A1 | 3/2002 | Edwards et al. | 2007/0093801 A1 | 4/2007 | Behnke |
| 2002/0035364 A1 | 3/2002 | Schoenman et al. | 2007/0135812 A1 | 6/2007 | Sartor |
| 2002/0052599 A1 | 5/2002 | Goble | 2007/0173802 A1 | 7/2007 | Keppel |

| Pub. No. | Date | Inventor |
|---|---|---|
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 8/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 8/2000 |
| EP | 246350 | 11/1987 |
| EP | 310431 | 4/1989 |
| EP | 325456 | 7/1989 |
| EP | 336742 | 10/1989 |
| EP | 390337 | 10/1990 |
| EP | 556705 | 8/1993 |
| EP | 569130 | 11/1993 |
| EP | 608609 | 8/1994 |
| EP | 694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 3/2004 |
| EP | 1495712 | 1/2005 |
| EP | 1500378 | 1/2005 |
| EP | 1535581 | 6/2005 |
| EP | 1609430 | 12/2005 |
| EP | 1707144 | 3/2006 |
| EP | 1645235 | 4/2006 |
| EP | 880220 | 6/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1854423 | 11/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/06739 | 12/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO02/00129 | 1/2002 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |

| | | |
|---|---|---|
| WO | WO2005/060849 | 7/2005 |
| WO | WO2005/060365 | 11/2005 |
| WO | WO2006/050888 | 5/2006 |
| WO | WO2006/105121 | 10/2006 |

OTHER PUBLICATIONS

International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "Measurement of Physiologic Events by Electrical Impedance" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al. "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Muller et al. "Extended Left Hemicolectomy Using the LigaSure Vessel Sealing System" Innovations That Work; Sep. 1999.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07010673.7 dated Sep. 24, 2007.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
US 6,878,148, 04/2005, Goble et al. (withdrawn)

* cited by examiner

CONNECTOR SYSTEMS FOR ELECTROSURGICAL GENERATOR

This application is a Continuation Application which claims the benefit of and priority to of U.S. patent application Ser. No. 11/508,615, filed on Aug. 23, 2006, now U.S. Pat. No. 7,416,437 which is a continuation of U.S. application Ser. No. 10/718,114, filed Nov. 20, 2003, now U.S. Pat. No. 7,131,860, the entire contents of each of which are incorporated herein by reference.

BACKGROUND

1. Technical Field

The present disclosure relates to electrosurgical instrument systems and, more particularly, to connector systems for selectively connecting electrosurgical instruments and electrosurgical generators to one another.

2. Background

Electrosurgical instrument systems have become widely used by surgeons in recent years. Accordingly, a need has developed for equipment that is easy to handle and operate, is reliable and is safe. By and large, most electrosurgical instrument systems typically include a hand-held electrosurgical instrument or pencil electrically connected to a source of electrosurgical energy (e.g., an electrosurgical generator). The electrosurgical instrument transfers radio-frequency (RF) electrical energy to a tissue site. The electrosurgical energy is returned to the electrosurgical generator via a return electrode pad positioned under a patient (i.e., a monopolar system configuration) or a smaller return electrode positionable in bodily contact with or immediately adjacent to the surgical site (i.e., a bipolar system configuration). The waveforms produced by the electrosurgical generator yield a predetermined electrosurgical effect known generally as electrosurgical fulguration.

Recently, electrosurgical instrument systems have been increasingly provided with coupling and/or connecting systems (e.g., a plug) for removably connecting the electrosurgical instrument to the electrosurgical generator. Typically, the electrosurgical instrument is provided with a so called "male" connector while the electrosurgical generator is provided with the corresponding "female" connector.

Since electrosurgery requires controlled application of radio frequency energy to an operative tissue site, it is important that the appropriate electrosurgical generator be correctly and/or properly mated with the electrosurgical instrument for the specific electrosurgical procedure. Due to the variety of operative, electrosurgical procedures, requiring various levels of radio frequency energy delivery from an attached instrument, issues arise with the mismatching of electrosurgical instruments and electrosurgical generators.

Accordingly, a need exists for a connecting system, for electrosurgical generators which allow various surgical instruments to be selectively connected to corresponding electrosurgical generators.

SUMMARY

The present disclosure relates to connector systems for connecting an electrosurgical instrument to an electrosurgical generator. According to one particularly advantageous embodiment of the present disclosure, the connector system includes a plug portion connected to the electrosurgical instrument and including a profile or shape which is selectively mateable with a plug receptacle portion. Advantageously, the plug receptacle portion is retained in the electrosurgical generator and is backward compatible, i.e., able to receive both old flying lead electrosurgical instruments or 2-pin, 3-pin or 4-pin electrical instruments and able to selectively receive enhanced surgical devices with multiple electrical connections.

In one embodiment, the plug portion includes a plug housing having a power pin extending therefrom. The power pin is advantageously positioned closer to a first side edge of the plug housing than a second side edge thereof, wherein the second side edge is opposite the first side edge.

Advantageously, the plug portion includes at least one position pin extending from the plug housing. Preferably, a first position pin extends from a center of the plug housing in substantially the same direction as the power pin. A second position pin may be included which extends from the plug housing at a location off-set from the center thereof and in the same direction as the power pin.

The connector system may also advantageously include a prong extending from the plug housing and substantially in the same direction as the power pin. The prong is desirably positioned closer to a first side edge of the plug housing than a second side edge thereof, wherein the second side edge is opposite the first side edge thereof.

The prong preferably includes a plurality of electrical contacts which provide electrical continuity to the electrosurgical generator. In one embodiment, the prong has a generally L-shaped cross-sectional profile for use with a six (6) contact electrosurgical system. In another embodiment, the prong has a generally rectilinear cross section or profile for use with a four (4) contact system. Advantageously, the L-shaped cross-sectional profile blocks insertion of a plug portion into the plug receptacle portion which is upside down. Other shapes are also envisioned, e.g., generally rectangular, for lesser contact systems, e.g., a four (4) contact system.

Preferably, the plug receptacle portion is operatively retained in the electrosurgical generator and defines a recess for receipt of the plug portion therein. The plug receptacle portion advantageously includes a prong receptacle formed therein, the prong receptacle being shaped and dimensioned to receive the prong therein. It is envisioned that the plug receptacle portion can include a plurality of apertures formed therein for receiving the power pin and the position pins. Preferably, each aperture includes a contact terminal operatively associated therewith. The plug receptacle portion advantageously includes at least one contact pin extending therethrough which is positioned to contact a respective one of the electrical contacts of the prong.

The prong desirably has an overall width which is less than about 0.43 inches and an overall height which is less than about 0.38 inches for the L-shaped six (6) contact prong. For prongs with less than six (6) contacts, e.g., four (4) contacts, the overall height may be less. The prong receptacle desirably has an overall width which is greater than about 0.39 inches and an overall height which is greater than about 0.324 inches.

In one embodiment of the connector system, the connector system includes a tactile feedback mechanism which provides positive tactile feedback to the user that the plug portion has been properly inserted into the plug receptacle portion. Advantageously, the tactile feedback mechanism includes a first post extending through and pivotally supported on the plug receptacle portion and a second post extending through and supported on the plug receptacle portion. Preferably, the first post is spring biased. The tactile feedback mechanism also includes a linkage member which extends between the first post and the second post. The linkage member includes a first arm which extends radially from the first post and a second arm which is supported on and extends from the second post.

A camming pin extends through a distal end of the first arm. The camming pin preferably includes a first portion slidably receivable in an elongate slot formed in the second arm. A second portion is slidably received in an arcuate slot formed in the prong receptacle. The second portion is extendable to engage a groove formed in a lower surface of the prong. A spring is positioned to bias the first portion to a distal-most position in the elongate slot.

In one embodiment, the plug portion includes symbology provided on a surface thereof which includes information regarding the operative parameters of the electrosurgical instrument.

The present disclosure also relates to a connector system for connecting an electrosurgical instrument to an electrosurgical generator which includes a plug portion and a plug receptacle portion disposed on the generator. The plug portion includes a plurality of mechanical interfaces which selectively mate with a corresponding plurality of mechanical interfaces in the plug receptacle portion. A tactile feedback mechanism is included for providing positive feedback to the user that the mechanical interfaces of the plug portion have been properly mated with the corresponding mechanical interfaces of the plug receptacle portion.

The tactile feedback mechanism includes a pair of first and second posts extending through and pivotally supported on the plug receptacle portion and a linkage member extending between the first post and the second post. The linkage member has a first arm extending radially from the first post and a second arm supported on and extending from the second post. A camming pin is included which extends through a distal end of the first arm. Upon insertion of the plug portion into the receptacle portion, the camming pin rides along a slot disposed in the second arm to initially compress a spring. After a predetermined point of the camming pin riding along the slot, the spring subsequently expands to drive the camming pin through the slot thus towing the prong portion into prong receptacle portion.

Other objects and features of the present disclosure will become apparent from consideration of the following description taken in conjunction with the accompanying drawings.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

DETAILED DESCRIPTION

Figure 1:
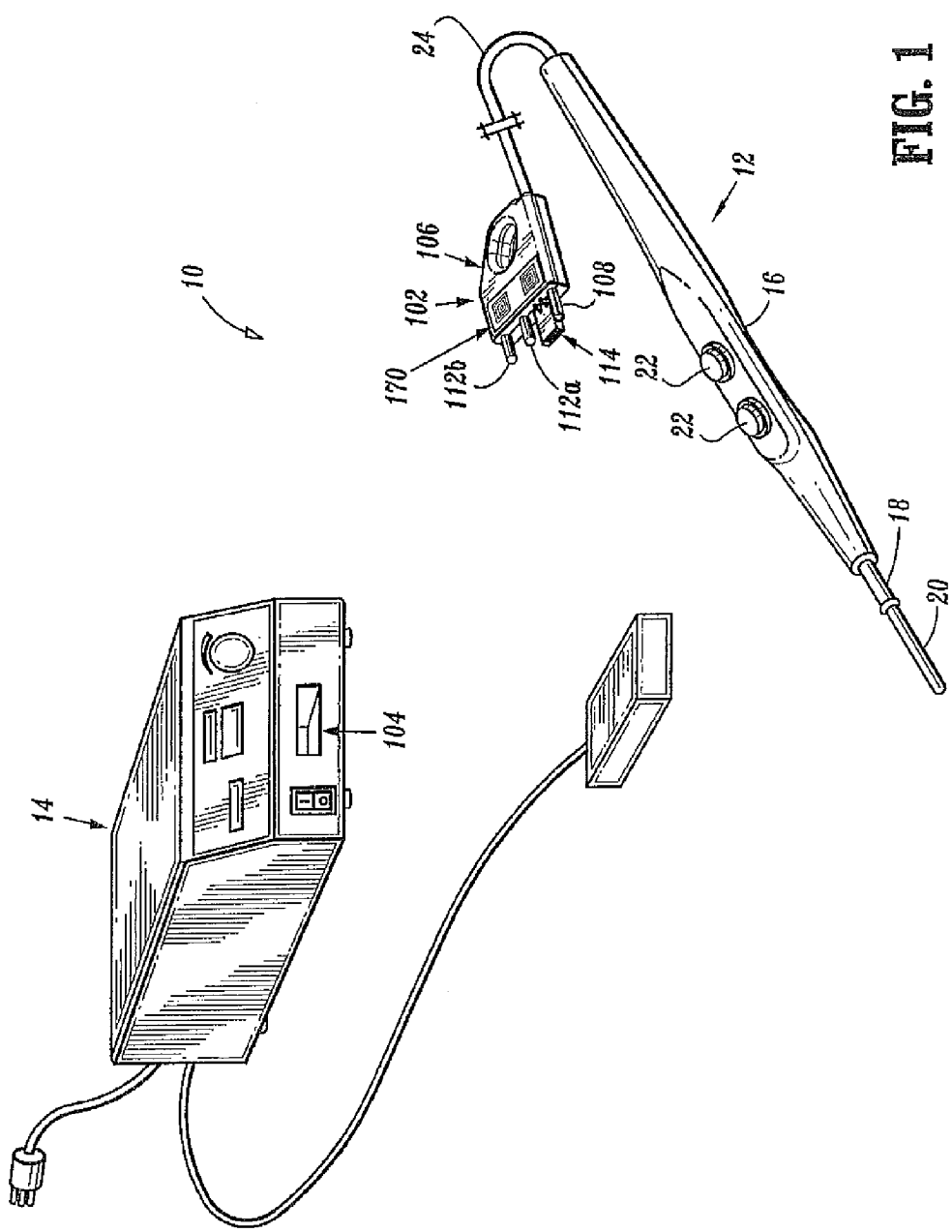
FIG. 1 is a schematic illustration of an electrosurgical instrument system in accordance with the present disclosure.

Embodiments of the presently disclosed connector system for electrosurgical generators are described in detail herein with reference to the drawing figures wherein like reference numerals identify similar or identical elements. In the drawings and in the description which follows, the term "proximal", as is traditional, will refer to the end of the apparatus and/or device which is closest to the operator, while the term "distal" will refer to the end of the apparatus and/or device which is furthest from the operator.

Referring initially to FIG. 1, there is seen a perspective view of an electrosurgical instrument system in accordance with an exemplary embodiment of the present disclosure, generally indicated as reference numeral 10. Electrosurgical instrument system 10 includes an electrosurgical instrument 12 (e.g., an electrosurgical pencil) which is electrically connectable to a source of electrosurgical energy 14 (e.g., an electrosurgical generator).

Electrosurgical pencil 12 includes a housing 16 configured and adapted to support a blade receptacle 18 at a distal end thereof which, in turn, receives a replaceable electrocautery blade 20 therein. Electrosurgical pencil 12 further includes at least one activation button 22 supported on an outer surface of housing 16. Activation button(s) 22 are operable to control the supply of RF electrical energy to blade 20 from electrosurgical generator 14.

By way of example only, electrosurgical generator 14 may be any one of the following, or equivalents thereof: the "FORCE FX", "FORCE 2" or "FORCE 4" generators manufactured by Valleylab, Inc. of Boulder, Colo. It is contemplated that electrosurgical generator 14 can be preset to selectively provide an appropriate first predetermined RF signal (e.g., about 1 to 300 watts) for tissue cutting and an appropriate second predetermined RF signal (e.g., about 1 to 120 watts) for tissue coagulation. However, as will be described in greater detail below, electrosurgical generator 14 preferably is adapted to automatically configure itself to transmit particular RF signals depending on the particular electrosurgical instrument connected thereto.

As seen in FIGS. 1-9, electrosurgical instrument system 10 is provided with a connector system 100, as best seen in FIG.

2, which is configured and adapted to selectively connect particular electrosurgical instruments (e.g., electrosurgical pencils 12) to particular sources of electrosurgical energy (e.g., electrosurgical generators 14). Connector system 100 includes a plug or male portion 102 operatively associated with electrosurgical instrument 12 via a connecting wire 24 and a receptacle, socket or female portion 104 which is operatively associated with electrosurgical generator 14. Preferably, receptacle portion 104 is "backward compatible", i.e., able to receive or connect to plug portions 102 of the various electrosurgical instruments disclosed herein as well as able to receive or connect other prior electrosurgical instruments which include less pins or prongs.

Figure 4:
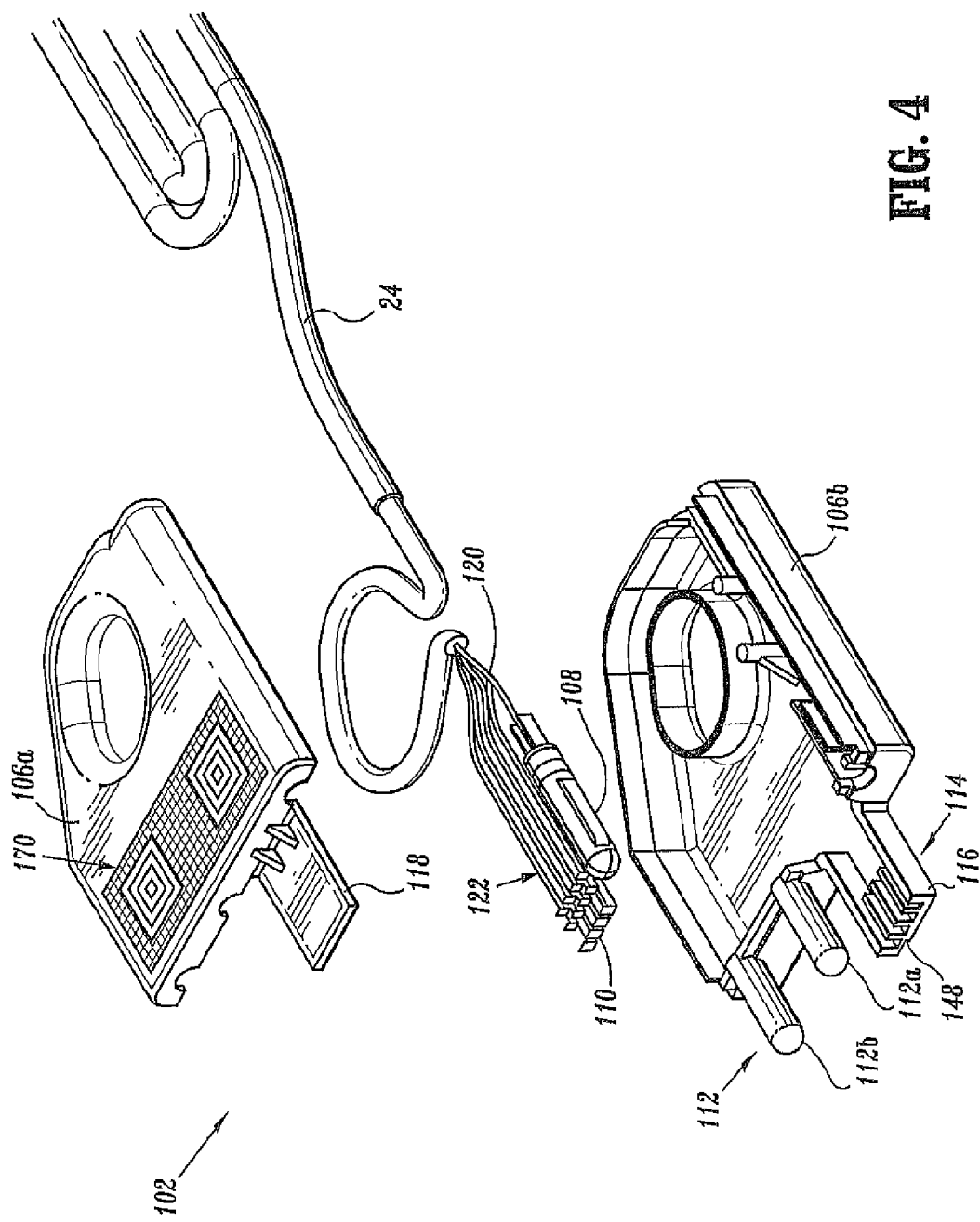
FIG. 4 is an enlarged exploded perspective view of the plug portion of the connector system of FIGS. 2-3.

With reference to FIG. 4, plug portion 102 includes a housing portion 106 having a first-half section 106a and a second half-section 106b operatively engagable with one another, preferably, via a snap-fit engagement. Half-sections 106a, 106b are configured and adapted to retain a common power pin 108 and a plurality of electrical contacts 110 therebetween, as will be described in greater detail below.

Plug portion 102 includes a power pin 108 extending distally from housing 106 at a location preferably between first half-section 106a and second half-section 106b. Preferably, power pin 108 is positioned to be off center, i.e., closer to one side edge of housing 106 than the other. Plug portion 102 further includes at least one, preferably, a pair of position pins 112 also extending from housing 106. Position pins 112 are preferably positioned between half-sections 106a and 106b and are oriented in the same direction as power pin 108. Desirably, a first position pin 112a is positioned in close proximity to a center of housing 106 and a second position pin 112b is positioned to be off center and in close proximity to an opposite side edge of housing 106 as compared to power pin 108. Pins 112a, 112b and 108 are preferably located on plug portion 102 at positions which correspond to the pin positions of earlier connections which are compatible to earlier known generators.

Plug portion 102 further includes a prong 114 extending from housing 106. In particular, prong 114 includes a body portion 116 (see FIG. 4) extending from second half-section 106b of housing 106 and a cover portion 118 extending from first half-section 106a of housing 106. In this manner, when half-sections 106a, 106b are joined to one another, cover portion 118 of prong 114 encloses body portion 116. Preferably, prong 114 is positioned between power pin 108 and first position pin 112a. Prong 114 is configured and adapted to retain electrical contacts 110 therein such that a portion of each contact 110 is exposed along a front or distal edge thereof. While four contacts 110 are shown, it is envisioned that any number of contacts 110 can be provided, including and not limited to two, six and eight. Prong 114 is dimensioned to have an overall width which is less than about 0.43 inches and an overall height which is less than about 0.38 inches.

With continued reference to FIG. 4, connecting wire 24 includes a power supplying wire 120 electrically connected to power pin 108 and a plurality of control wires 122 electrically connected to contacts 110.

Figure 2:
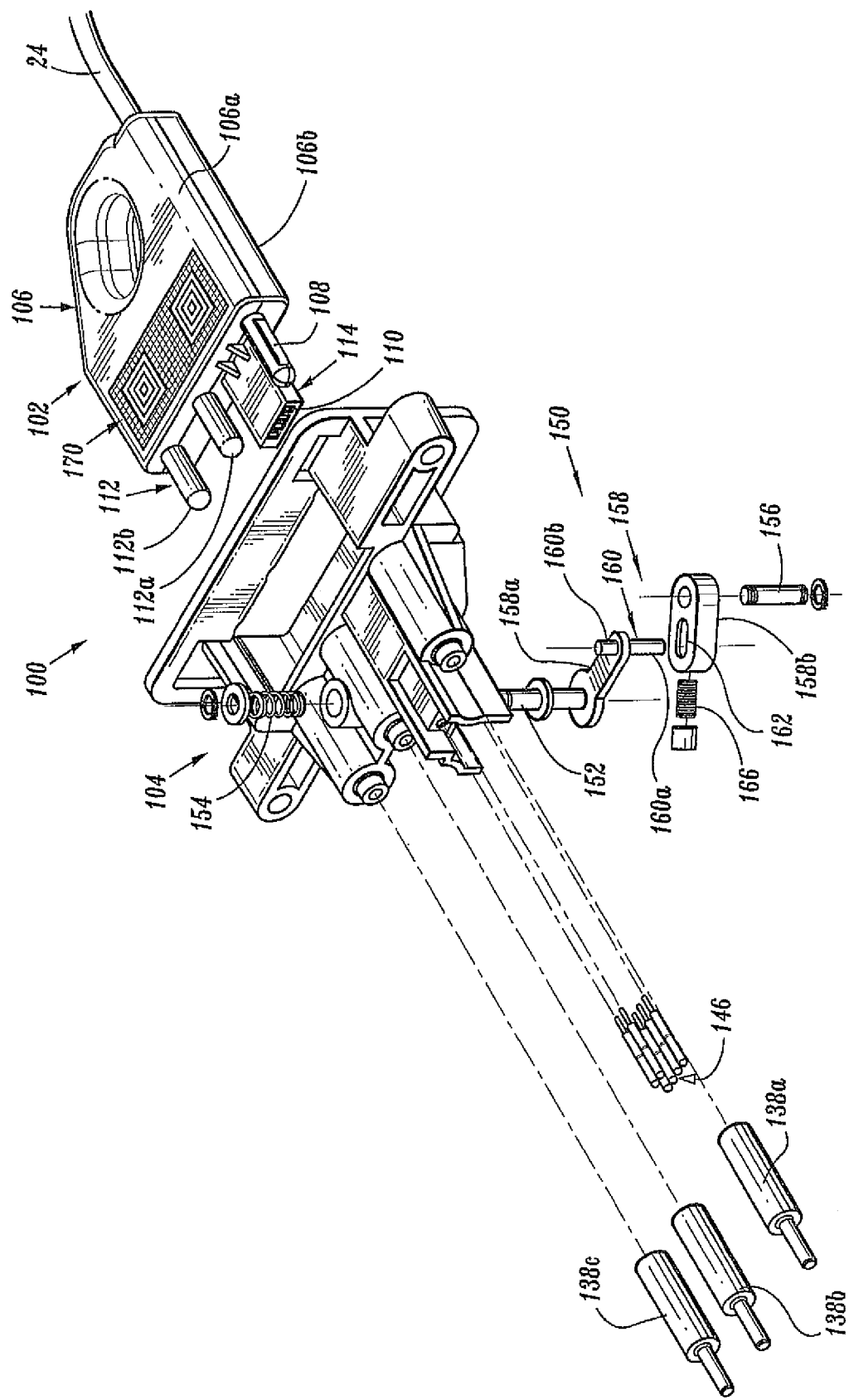
FIG. 2 is an enlarged perspective view of a connector system, in accordance with an embodiment of the present disclosure, as seen from above.
Figure 5:
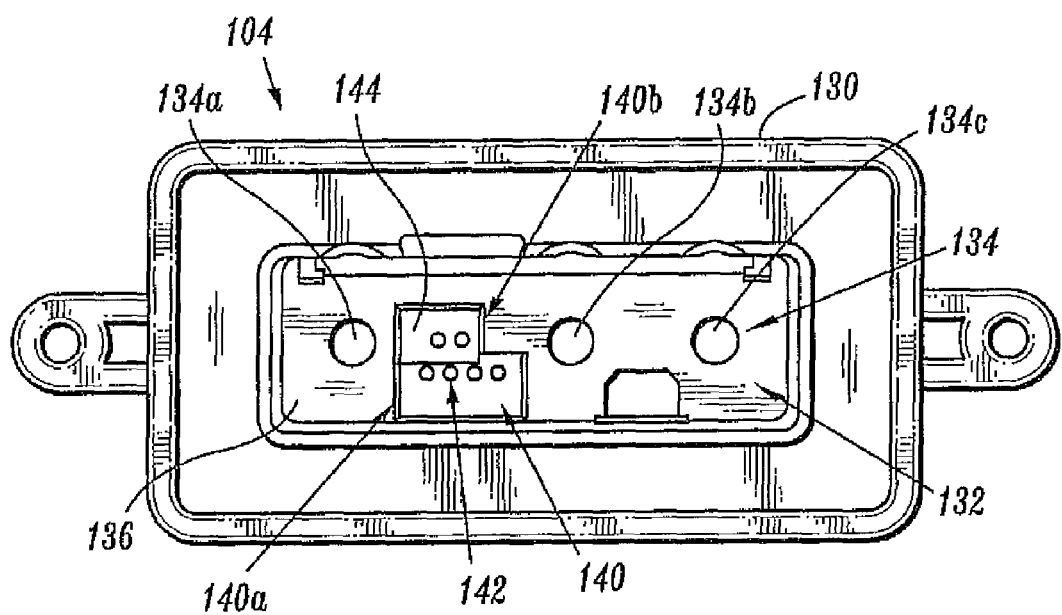
FIG. 5 is a front elevational view of the receptacle portion of the connector system of FIGS. 2-3.
Figure 6:
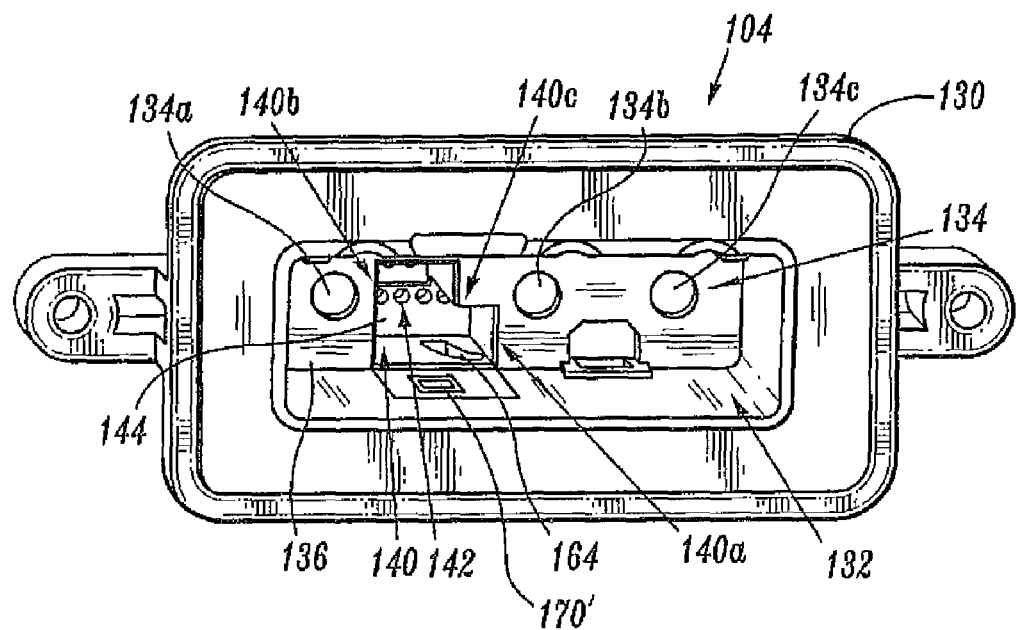
FIG. 6 is a front perspective view of the receptacle portion of the connector system of FIGS. 2-3.

With reference to FIGS. 2 and 5-6, receptacle portion 104 of connector system 100 includes a housing 130 having a recess 132 formed therein. Recess 132 is configured and dimensioned to receive plug portion 102 therein. Recess 132 includes a plurality of apertures 134 formed in a rear wall 136 thereof. Preferably, three apertures 134a-134c are provided. Apertures 134a-134c are preferably positioned and sized to respectively receive power pin 108 and position pins 112 therein when plug portion 102 is inserted into receptacle portion 104. As mentioned above, preferably, apertures 134a-134c are positioned to receive connector pins from prior known connectors to enable the connector system to be backward compatible.

Figure 7:
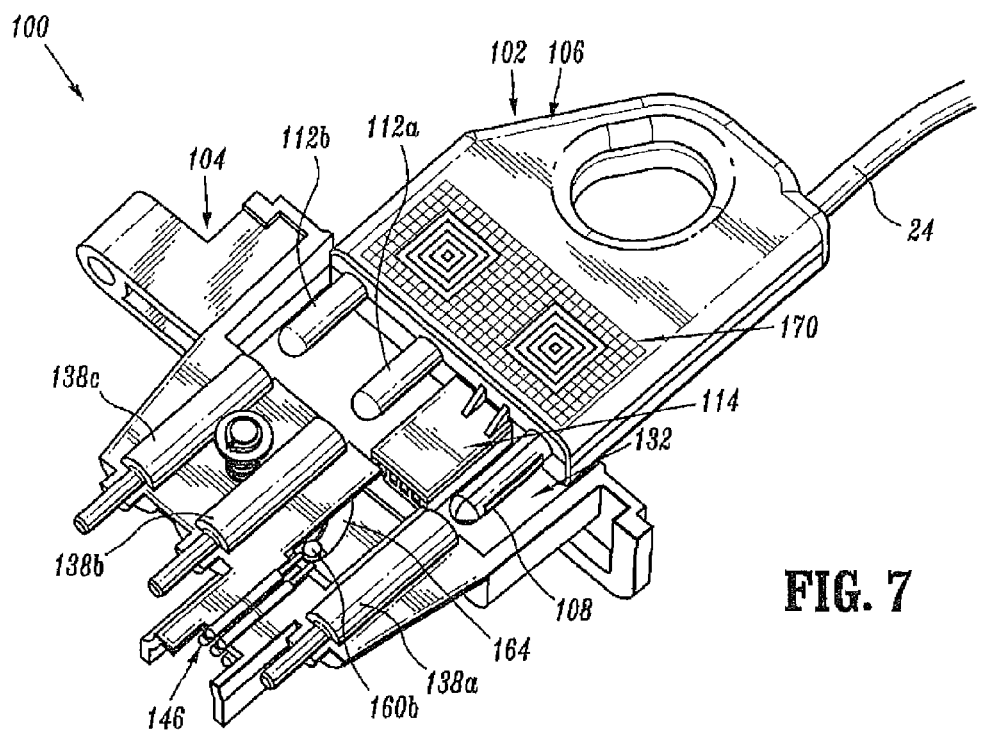
FIG. 7 is an enlarged top perspective view of connector system of FIGS. 2-3, with portions of the receptacle portion cut away, illustrating the mating and/or joining of the plug portion with the receptacle portion.
Figure 8:
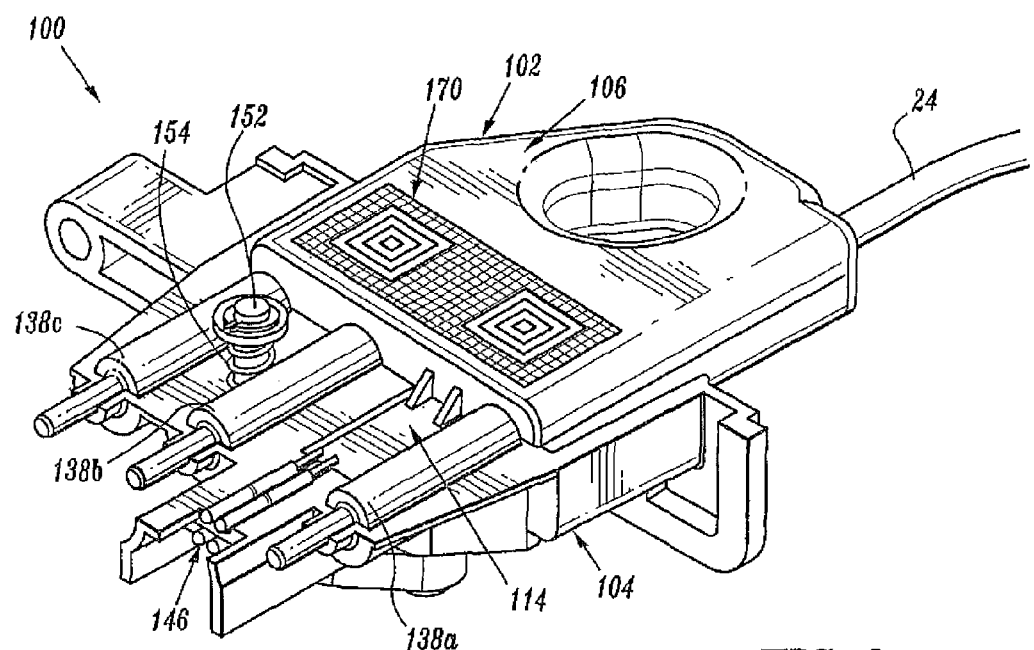
FIG. 8 is an enlarged top perspective view of the connector system of FIGS. 2-3, with portions of the receptacle portion cut away, illustrating the plug portion mated with the receptacle portion.
Figure 9:
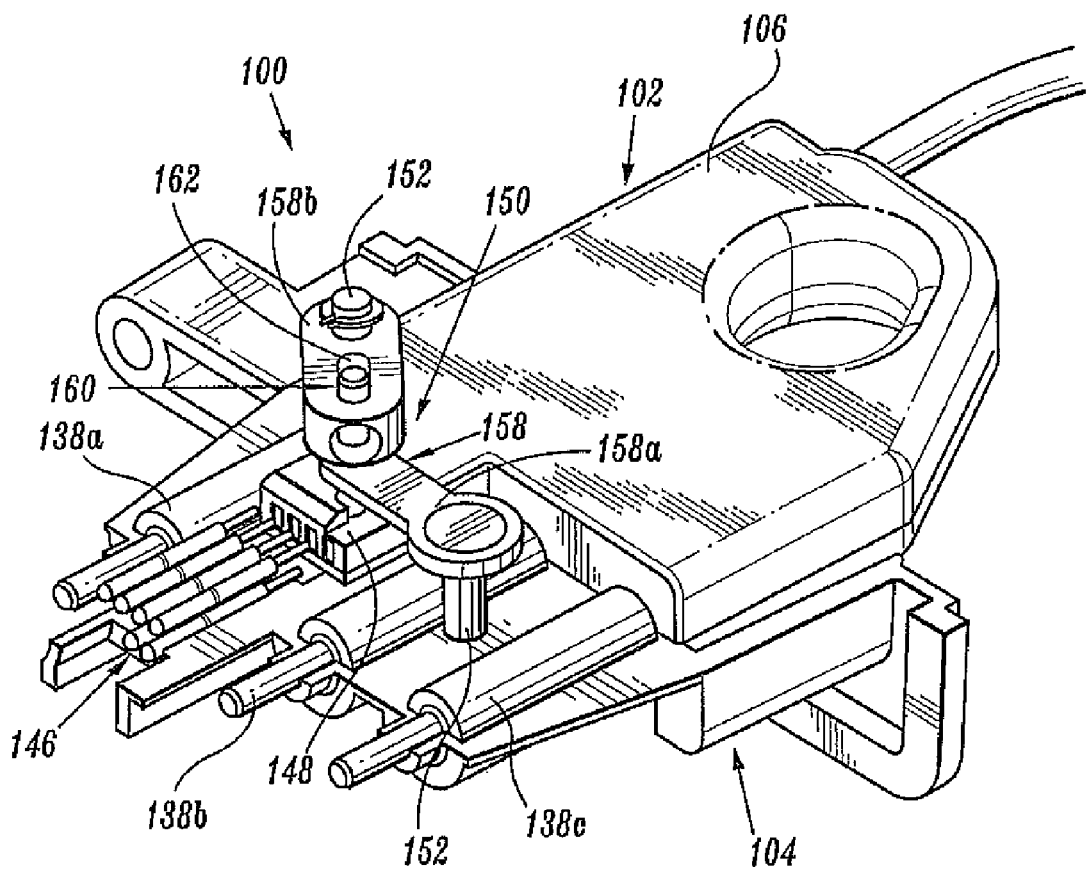
FIG. 9 is an enlarged bottom perspective view of the connector system of FIGS. 2-3, with portions of the receptacle portion broken away, illustrating the plug portion mated with the receptacle portion.

As seen in FIG. 2, and in greater detail in FIGS. 7-9, receptacle portion 104 further includes contact terminals 138a-138c disposed behind rear wall 136 and in registration with a respective aperture 134a-134c. Contact terminals 138a-138c are configured and dimensioned to receive power pin 108 and position pins 112 therein. While only contact terminal 138a needs to be configured and adapted to create an electrical interface with power pin 108, it is within the scope of the present disclosure to have each contact terminal 138a-138c configured and adapted to provide electrical interfaces. For example, contact terminals 138a-138c can be fabricated from an electrically conductive material such that when plug portion 102 is inserted into receptacle portion 104 and power pin 108 is inserted into corresponding contact terminal 138a through aperture 134a, contact terminal 138a electrically engages power pin 108 and, in turn, enables transmission of RF energy from electrosurgical generator 14 to electrosurgical instrument 12. One practicable example would be to utilize the positive engagement of pins 112a, 112b within the contact terminals 138a, 138b as a safety mechanism, i.e., pins 112a, 112b must be properly and fully seated within terminals 138a, 138b to allow the generator to supply energy to the instrument.

With continued reference to FIGS. 5 and 6, receptacle portion 104 further includes a prong receptacle 140 formed in rear wall 136. Prong receptacle 140 is preferably formed between apertures 134a and 134b. Prong receptacle 140 is sized and shaped to receive prong 114 therein when plug portion 102 is inserted into receptacle portion 104.

Since prong 114 extends from second half-section 106b of housing 106 of plug portion 102, plug portion 102 will not enter receptacle portion 104 unless plug portion 102 is in the proper orientation. In this manner, it is ensured that power pin 108 is in electrical contact with corresponding contact terminal 138a. As can be appreciated, connectors which do not include prongs 114 are still connectable to receptacle portion 104 (i.e., backward compatible). However, electrical contacts 110 associated with prong 114 are designed to further enhance the electrical connection between the instrument and the generator and give the surgeon more feedback at the operative site. For example, commonly-owned and concurrently-filed U.S. patent application Ser. No. 11/640,673 entitled "ELECTROSURGICAL PENCIL WITH IMPROVED CONTROLS" and PCT Application Serial No. PCT/US03/22900 entitled "ELECTROSURGICAL PENCIL WITH DRAG SENSING CAPABILITY" describe several features which would typically utilize the additional electrical contacts 110 in prong 114 to enhance feedback to the surgeon at the operative site, e.g., mode or power settings or sensors for movement, position, drag or temperature.

Preferably, as seen in FIGS. 5 and 6, prong receptacle 140 includes a lower portion 140a configured and dimensioned to receive prong 114, as described above. Prong receptacle 140 is dimensioned to have an overall width which is greater than about 0.39 inches and an overall height which is greater than about 0.324 inches. It is envisioned that, prong receptacle 140 can further include an upper portion 140b which is integral with lower portion 140a and defines a prong receptacle 140 having an "L-shaped" cross-sectional profile. In this manner, prong receptacle 140 can receive prongs having any number of cross-sectional profiles, including and not limited to, rectangular (e.g. prong 114), square and "L-shaped" (see FIGS. 10 and 11). Moreover, "L-shaped" prong receptacle 140 defines a corner 140c which is shaped and sized to block the insertion of a traditional three pin plug when the traditional plug is being inserted upside down.

With continued reference to FIGS. 5 and 6, prong receptacle 140 includes a plurality of openings 142 formed in a rear wall 144 thereof for permitting passage of contact pins 146, preferably spring-type contact pins, therethrough. In this manner, when plug portion 102 is inserted into receptacle portion 104, electrical contacts 110 of prong 114 will electrically engage pins 146.

As best seen in FIG. 5, prong receptacle 140 can include four openings 142 formed in lower portion 140a and two openings 142 formed in upper portion 140b. While such an arrangement is shown and described, it is within the scope of the present disclosure to include various other arrangements including various numbers of pins 146.

With reference to FIGS. 2-9, connector system 100 further includes a tactile feedback mechanism 150 (see FIG. 9) for securing plug portion 102 into receptacle portion 104, for providing positive feedback to the user that plug portion 102 has been fully inserted into receptacle portion 104, and for compensating for increasing resistance that exists as prong 114 enters into prong receptacle 140 and engages pins 146.

Tactile feedback mechanism 150 includes a first post 152 extending through and pivotally supported on receptacle portion 104. Preferably, first post 152 is spring biased by a spring member 154. Tactile feedback mechanism 150 further includes a second post 156 extending through and supported on receptacle portion 104. A linkage member 158 extends between first post 152 and second post 156. Linkage member 158 includes a first arm 158a extending radially from first post 152 and a second arm 158b supported on and extending from second post 156.

Figure 3:
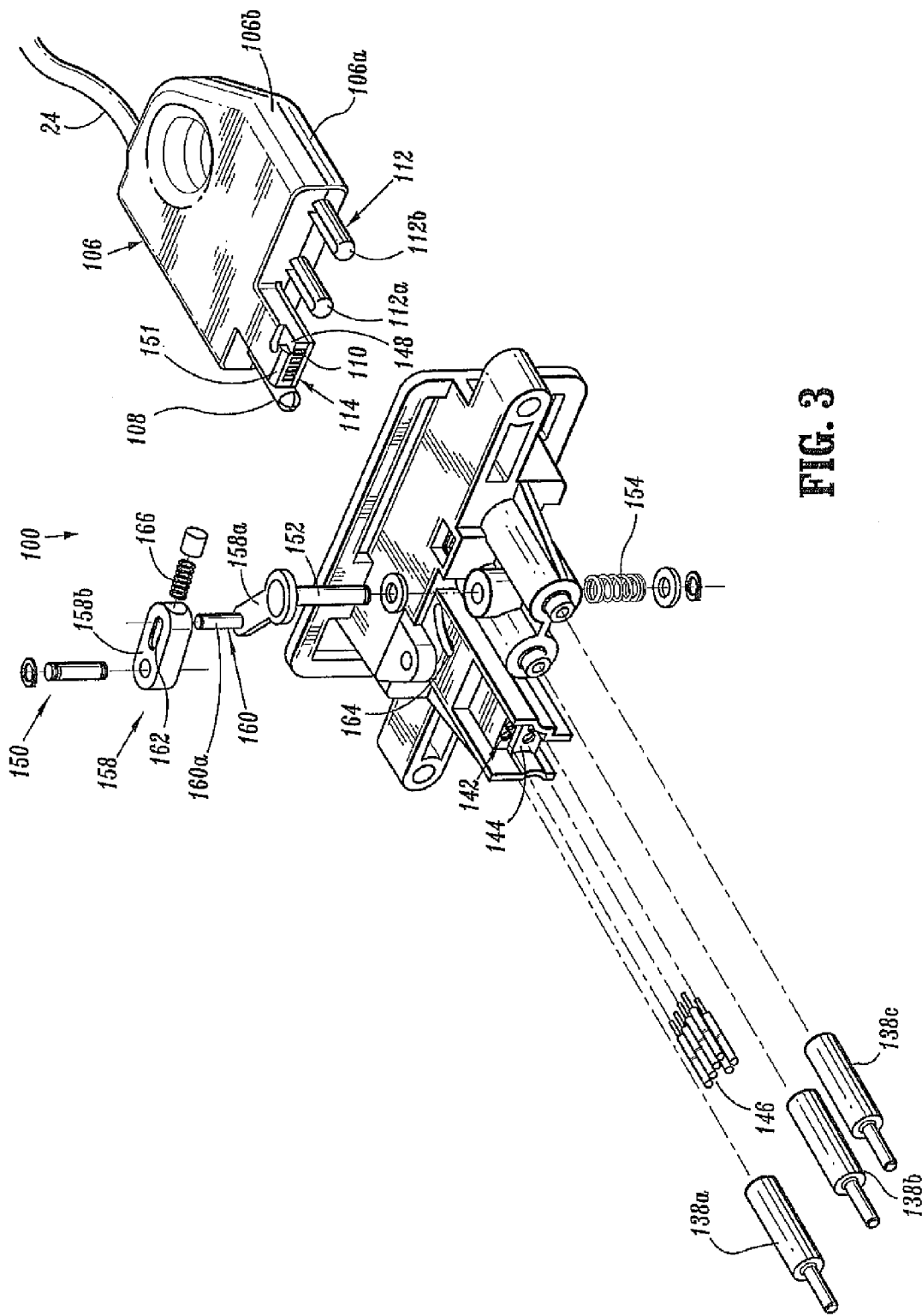
FIG. 3 is an enlarged perspective view of the connector system of FIG. 2, as seen from below.

A camming pin 160 extends through a distal end of first arm 158a and incluldes a first portion 160a which is slidably receivable in an elongate slot 162 (see FIG. 2) formed in second arm 158b and a second portion 160b, extending in an opposite direction to first portion 160a, which is slidably receivable in an arcuate slot 164 formed in prong receptacle 140 (see FIGS. 3, 6 and 7). First portion 160a is biased to the distal-most position of elongate slot 162 by a spring 166 disposed within second arm 158b. Second portion 160b extends through arcuate slot 164 an amount sufficient to be engagable with an "L-shaped" groove and/or recess 148 formed in a lower surface of prong 114 (see FIGS. 3, 4 and 9) in order to define a bayonet-type engagement. Alternatively, second arm 158b may extend "opposite" first post 152 and be joined by a tension spring (not shown) to first post 152.

In use, with camming pin 160 initially positioned near the entrance of prong receptacle 140, as prong 114 enters prong receptacle 140, second portion 160b of camming pin 160 enters into and engages groove 148 of prong 114. As prong 114 is further advanced, camming pin 160 rides along arcuate slot 164 and elongate slot 162, thereby compressing spring 166. Once prong 114 is advanced beyond a point of criticality, spring 166 expands and thus drives camming pin 160 through the remainder of arcuate slot 164 thereby drawing prong 114 into prong receptacle 140.

It is envisioned that spring 154 may provide an additional safety feature as well. For example, spring 154 is provided in pin 152 to allow a mating chamfer 153 on pin 152 (FIG. 12) to ride up and over the chamfer 151 (FIG. 3) on plug 102. This is necessitated to allow plug 102 to be inserted in the event that the cam is disengaged prior to being pulled back to the proximal position upon removal of the last plug 102 to have been inserted.

As seen in FIGS. 1, 2, 4 and 7-8, connector system 100 further includes symbology 170 provided on a surface of plug portion 102, preferably on an outer surface of first half-section 106a of housing 106. Symbology 170 can include and is not limited to at least one of the following: bar codes, UPC codes, Postnet. Data Matrix, Maxi Code, Aztec Code and the like. Preferably, symbology 170 includes at least one Aztec code, preferably, a pair of Aztec codes positioned side-by-side.

Aztec Code is a high density two dimensional matrix style bar code symbology that can encode up to 3750 characters from the entire 256 byte ASCII character set. The Aztec code symbol is built on a square grid with a bulls-eye pattern at its center. Data is encoded in a series of "layers" that circle around the bulls-eye pattern. Each additional layer completely surrounds the previous layer thus causing the symbol to grow in size as more data is encoded yet the symbol remains square.

In this manner, each electrosurgical instrument 12 is provided with a characteristic symbology 170 containing information regarding the operative parameters for that particular electrosurgical instrument, such as, for example, the operative REF energy setting, the operative waveform setting, and the algorithm for interpreting signals on contact(s) 110 and pin(s) 146.

Connector system 100 can further include a symbology reader and/or scanner (not shown) operatively supported in receptacle portion 104. Accordingly, when plug portion 102 is mated with receptacle portion 104, the reader scans and reads the operative parameters contained in the characteristic symbology 170 and transmits the operative parameters to electrosurgical generator 14 which in turn automatically configures and/or sets itself to supply operative parameters (e.g., preset ranges, preferred settings and the like) to electrosurgical instrument 12. Alternatively, electrosurgical generator 14 can be engaged with a data table which, once the instrument is identified, will transmit the appropriate REF parameter to the identified instrument. In addition, as described above, symbology 170 can also be used as a positive engagement mechanism. For example, the symbology must be aligned or in a position to allow the instrument to operate or to allow the instrument to operate in an enhanced mode.

For example and with respect to FIG. 6, receptacle 140 may contain additional symbology 170' on the interior surface opposite the scanner window similar to that on plug 12. The symbology 170' is positioned between the power pin and the next adjacent pin. The scanner will then read the symbology 170' whenever a plug is not inserted. When a plug is inserted, the symbology 170' will be blocked and the scanner will then read the symbology 170 on the plug 102 to determine pencil type and the appropriate electrosurgical settings associated that that particular pencil. If the symbology 170' is blocked but no new symbology 170 is identified, then the generator will determine that the plug 102 is of an old style pencil without enhanced capabilities (e.g., an E2525 or E2516 Electrosurgical Pencil sold by Valleylab—a division of Tyco Healthcare LP in Colorado). Old style pencils will respond to switch signals on pins 138b and 138c outputting RF on a pin 138 as called for by the surgeon. The symbology 170' in the receptacle is preferably positioned such that flying leads from existing devices will not obscure the symbology 170' and therefore will not enable the electrosurgical generator to output RF through pin 108.

It is envisioned that connector system 100 can include a positive engagement mechanism configured and adapted to ensure proper engagement of prong portion 102 in receptacle portion 104 prior to allowing activation of electrosurgical instrument 12. For example, the positive engagement mechanism may include an optical coupler pair (e.g., an optical coupler member operatively associated with prong portion 102 and a cooperating coupler member operatively associated with receptacle portion 104, for example, reflective diodes), mechanical coupler pairs, electro-mechanical coupler pairs, and/or bar code readers. In addition, the positive engagement mechanism can be configured and adapted to not be activated and/or triggered by insertion of "flying leads", from prior art instruments, into receptacle portion 104 thereby preventing activation of such instruments.

Figure 10:
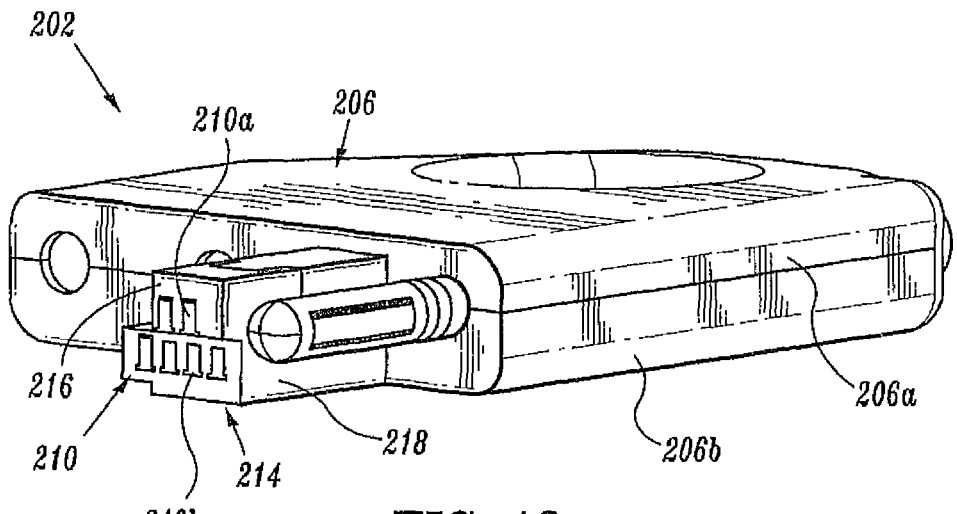
FIG. 10 is a perspective view of a plug portion in accordance with an alternate embodiment of the present disclosure, as seen from above.
Figure 11:
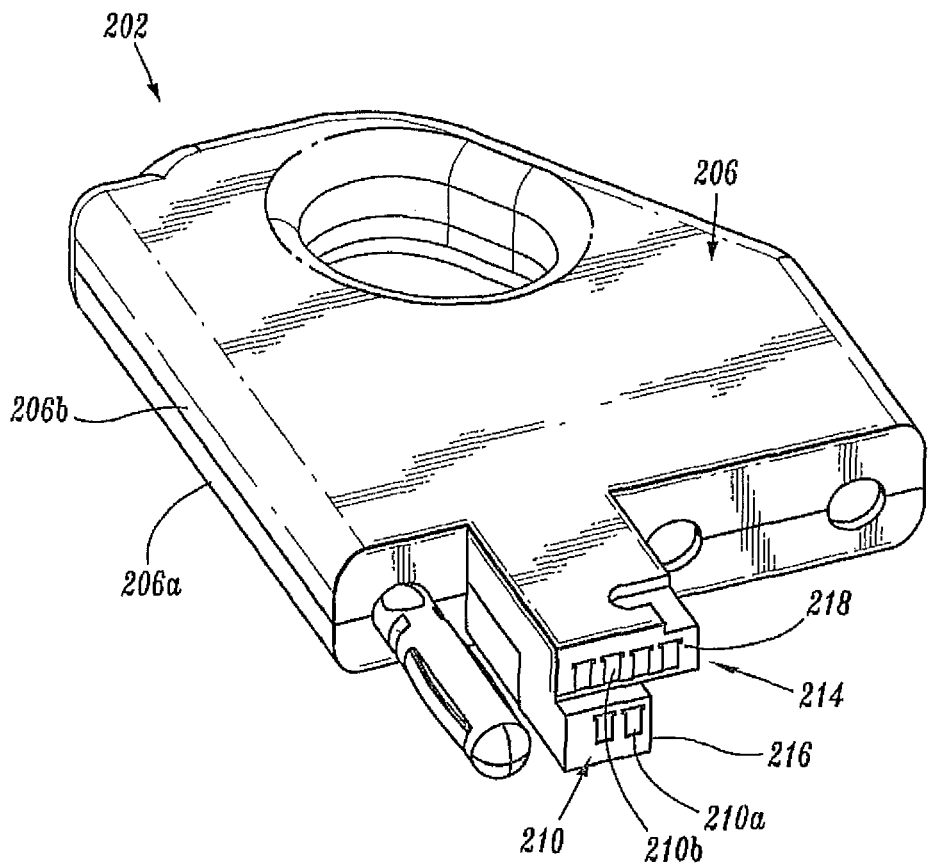
FIG. 11 is a perspective view of the plug portion of FIG. 10 as seen from below.

Turning now to FIGS. 10 and 11, a plug portion, in accordance with an alternate embodiment of the present disclosure, is designated generally as 202. Plug portion 202 is similar to plug portion 102 and will only be described in detail to the extent necessary to identify differences in construction and/or operation.

Plug portion 202 includes a prong 214 extending from housing 206. In particular, prong 214 includes a first portion 216 extending from first half-section 206a of housing 206 and a second portion 218 extending from second half-section 206b of housing 206. Preferably, second portion 218 of prong 214 has a width which is greater than a width of first portion 216. In this manner, when first and second half-sections 206a, 206b of housing 206 are joined to one another, prong 214 has an L-shaped transverse cross-sectional profile. In particular, prong 214 is configured and dimensioned to be received in complementary shaped prong receptacle 140 of receptacle portion 104 (see FIGS. 4 and 5).

Prong 214 includes a plurality of contacts 210 exposed along a front surface thereof. In particular, prong 214 includes a first set of contacts 210a, preferably two, exposed along a front surface of first portion 216 of prong 214 and a second set of contacts 210b, preferably, four, exposed along a front surface of second portion 218 of prong 214.

Accordingly, the first set of contacts 210a electrically engage pins 146 extending from openings 142 formed in upper portion 140b of prong receptacle 140. In addition, the second set of contacts 210b electrically engage pins 146 extending from opening 142 formed in lower portion 140a of prong receptacle 140.

Figure 12:
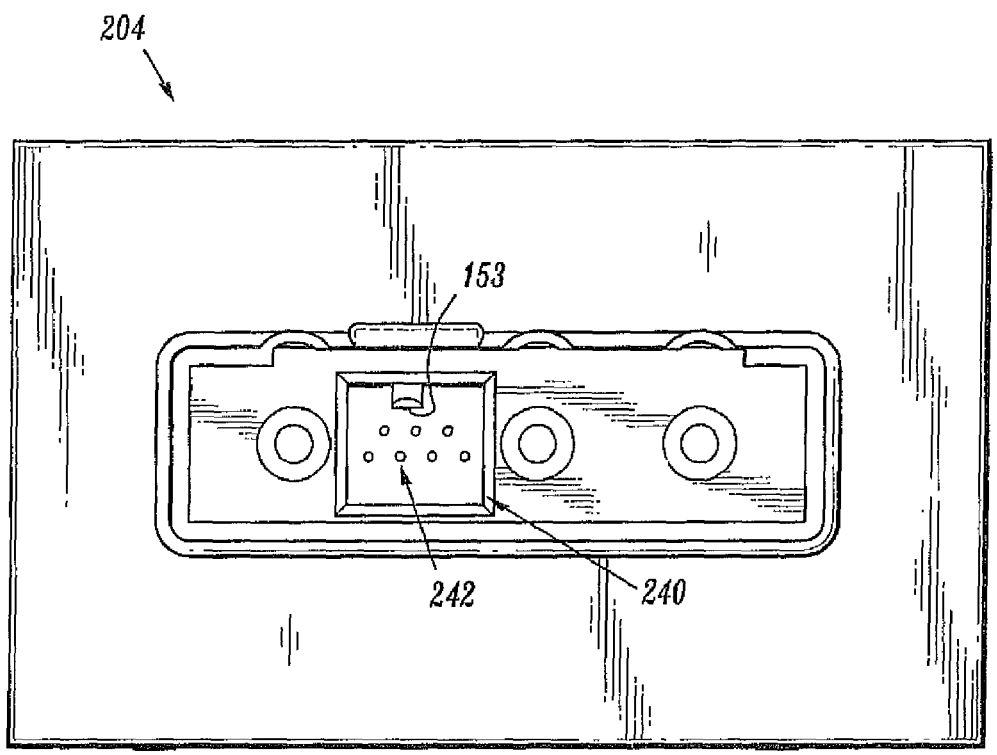
FIG. 12 is a front elevational view of a receptacle portion according to an alternate embodiment of the present disclosure.
Figure 13:
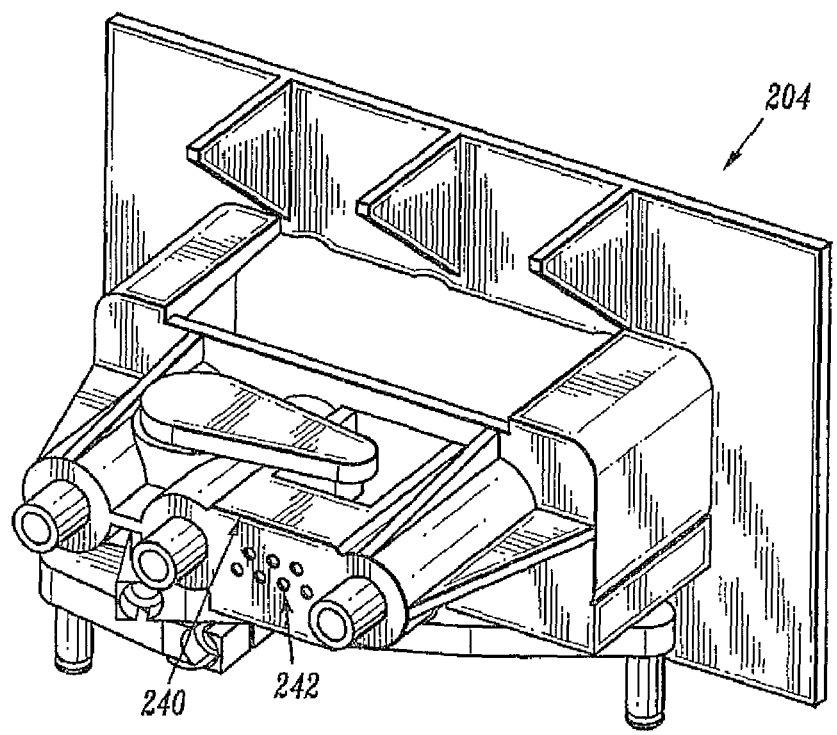
FIG. 13 is a rear perspective view of the receptacle portion of FIG. 12.

Turning now to FIGS. 12 and 13, a receptacle portion, in accordance with an alternate embodiment of the present disclosure, is designated generally as 204. Receptacle portion 204 is similar to receptacle portion 104 and will only be described in detail to the extent necessary to identify differences in construction and/or operation.

Receptacle portion 204 includes a prong receptacle 240 having a substantially rectilinear cross-sectional profile. Prong receptacle 240 is configured and dimensioned to receive prong 114 and/or prong 214 therein. Prong receptacle 240 includes a plurality of openings 242 formed in a rear wall 244 thereof. Preferably, two rows of openings 242 are formed, a first row including three openings and a second row including four openings. A pin 146 (not shown) can extend from each opening 242 for electrical engagement with contacts 210.

Figure 14:
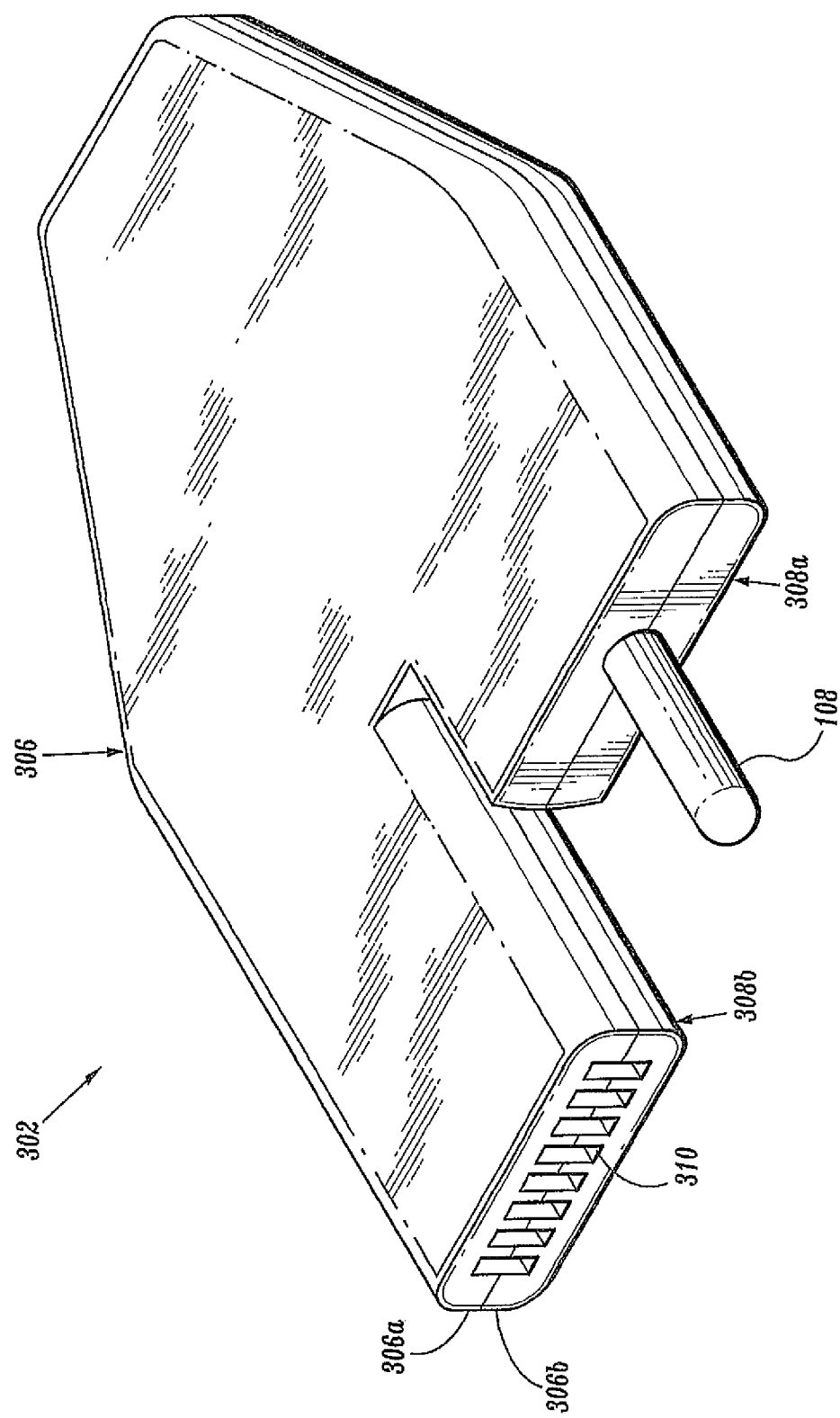
FIG. 14 is a perspective view of a plug portion in accordance with yet another embodiment of the present disclosure.

Turning now to FIG. 14, a plug portion, in accordance with yet another alternate embodiment of the present disclosure, is designated generally as 302. Plug portion 302 includes a housing 306 including a first half-section 306a and a second half-section 306b defining a plane therebetween. Housing 306 further includes a first side portion 308a and a second side portion 308b. Preferably, second side portion 308b has a length which is greater than a length of first side portion 308a.

As seen in FIG. 14, power pin 108 extends distally from first side portion 308a. Preferably, power pin 108 extends from first side portion 308a an amount sufficient such that a distal-most end of power pin 108 is substantially even with a distal-most surface of second side portion 308b.

Second side portion 308b includes a plurality of contacts 310 exposed along the distal-most surface thereof. In particular, second side portion 308b includes eight contacts 310 exposed along a distal-most surface thereof. Preferably, contacts 310 are in the same plane as power pin 108.

It is envisioned that electrosurgical generator 14 includes a receptacle portion (not shown) configured and dimensioned to receive and mate with plug portion 302.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

Those skilled in the art will envision other modifications within the scope and spirit of the claims appended hereto.

The invention claimed is:

1. A connector system for connecting an electrosurgical instrument to an electrosurgical generator, the connector system comprising:
    a plug portion connectable to the electrosurgical instrument, said plug portion including a plurality of pins and a prong that extend therefrom, said prong retaining one or more electrical contacts therein;
    a plug receptacle portion disposed within the generator, said plug receptacle portion defining a recess for receiving at least a portion of said plug portion therein, said plug receptacle portion including a plurality of apertures for receiving respective ones of said plurality of pins and a prong receptacle for receiving said prong, the plug receptacle having a generally arcuate slot defined therein; and
    a tactile feedback mechanism disposed within the generator and adapted for activation when the plug portion is inserted into the plug receptacle portion,
    wherein the tactile feedback mechanism is adapted to slidably engage a recess associated with the plug portion via a camming pin when the plug portion is inserted into the plug receptacle,
    wherein as the plug portion is advanced beyond a point of criticality within the plug receptacle a spring operably associated with the cam pin drives the cam pin through the generally arcuate slot thereby drawing the plug portion into the plug receptacle.

2. The connector system according to claim 1, wherein the tactile feedback mechanism is pivotably connected to the plug receptacle portion.

3. The connector system according to claim 1, wherein the plug portion includes a plug housing configured to receive a connecting wire therein, the connecting wire having a power pin extending therefrom.

4. The connector system according to claim 3, wherein the power pin is positioned closer to a first side edge of the plug housing than a second side edge thereof, wherein the second side edge is opposite the first side edge thereof.

5. The connector system according to claim 4, wherein the plug portion further includes at least one position pin extending from the plug housing.

6. The connector system according to claim 5, wherein a first position pin extends from the plug housing near the second side edge and in substantially the same direction as the power pin, and a second position pin extends from the plug housing at a location off-set from the center thereof and in the same direction as the power pin.

7. The connector system according to claim 3, wherein the prong is positioned closer to a first side edge of the plug housing than a second side edge thereof, wherein the second side edge is opposite the first side edge thereof.

8. The connector system according to claim 6, wherein the prong is positioned between the power pin and the second position pin.

9. The connector system according to claim 1, wherein the prong includes a plurality of electrical contacts.

10. The connector system according to claim 1, wherein the prong has a first geometry and said prong receptacle has a second geometry different from the first geometry which is matingly compatible with said first geometry of said prong.

11. The connector system according to claim 1, wherein the prong has at least one of a generally L-shaped cross-sectional profile and a rectilinear-shaped profile.

12. The connector system according to claim 1, wherein each aperture includes a contact terminal operatively associated therewith.

13. The connector system according to claim 1, wherein the prong receptacle has an L-shaped cross-sectional profile.

14. The connector system according to claim 13, wherein the L-shaped cross-sectional profile defines a corner that blocks insertion of a three pin plug into the plug receptacle when the three pin plug is being inserted upside down.

15. The connector system according to claim 12, wherein the plug receptacle portion includes at least one contact pin extending therethrough.

16. The connector system according to claim 15, wherein the contact pins are positioned to contact respective ones of the electrical contacts of the prong.

17. The connector system according to claim 16, wherein the prong has an overall width which is less than about 0.43 inches and an overall height which is less than about 0.38 inches.

18. The connector system according to claim 17, wherein the prong receptacle has an overall width which is greater than about 0.39 inches and an overall height which is greater than about 0.324 inches.

19. The connector system according to claim 1, wherein the tactile feedback mechanism provides positive feedback to the user that the plug portion has been properly inserted into the plug receptacle portion.

20. The connector system according to claim 2, wherein the plug portion includes symbology provided on a surface thereof.

21. The connector system according to claim 20, wherein the symbology includes information regarding the operative parameters of the electrosurgical instrument.

22. A connector system for coupling electrosurgical instruments to electrosurgical generators, the connector system comprising:
   a first plug portion connectable to a first electrosurgical instrument, the first plug portion of the first electrosurgical instrument having a first configuration;
   a plug receptacle portion supported on an electrosurgical generator, the plug receptacle portion being configured to receive the first plug portion of the first electrosurgical instrument and to receive a second plug portion of a second electrosurgical instrument that has a second configuration different than the first configuration of the first plug portion, the plug receptacle having a generally arcuate slot defined therein; and
   a tactile feedback mechanism disposed within the generator and adapted for activation when one of the first and second plug portion is inserted into the plug receptacle portion,
   wherein the tactile feedback mechanism is adapted to slidably engage a recess associated with the plug portion via a camming pin when the plug portion is inserted into the plug receptacle,
   wherein as the plug portion is advanced beyond a point of criticality within the plug receptacle a spring operably associated with the cam pin drives the cam pin through the generally arcuate slot thereby drawing the plug portion into the plug receptacle.

23. The connector system according to claim 22, wherein the tactile feedback mechanism is pivotably connected to the plug receptacle portion.

24. The connector system according to claim 22, wherein the one of the first and second plug portion further includes a prong having a particular shape extending therefrom.

25. The connector system according to claim 24, wherein the prong has an L-shaped cross-sectional profile and includes at least one electrical contact.

26. The connector system according to claim 25, wherein the plug receptacle portion includes a prong receptacle formed therein configured and dimensioned to receive the prong therein.

27. The connector system according to claim 26, wherein the prong receptacle includes at least one pin extending therefrom for contact with a corresponding electrical contact.

28. The connector system according to claim 22, wherein the tactile feedback mechanism provides positive feedback to the user that the one of the first and second first plug portion has been properly inserted into the plug receptacle portion.

29. The connector system according to claim 22, wherein the one of the first and second first plug portion includes symbology provided on a surface thereof, the symbology including information regarding the operative parameters of the first electrosurgical instrument.

30. The connector system according to claim 26, wherein the prong has an overall width which is less than about 0.43 inches and an overall height which is less than about 0.38 inches.

31. The connector system according to claim 26, wherein the prong receptacle is configured and dimensioned to block insertion of the second plug portion that is being inserted in an incorrect orientation.

* * * * *